(12) United States Patent
Butler

(10) Patent No.: US 6,869,393 B2
(45) Date of Patent: Mar. 22, 2005

(54) INSERTION DEVICE FOR AN ENDOSCOPE

(75) Inventor: John Butler, Blackrock (IE)

(73) Assignee: Atropos Limited, Galway (IE)

( * ) Notice: Subject to any disclaimer, the term of this patent is extended or adjusted under 35 U.S.C. 154(b) by 95 days.

(21) Appl. No.: 10/246,401

(22) Filed: Sep. 19, 2002

(65) Prior Publication Data

US 2003/0069472 A1 Apr. 10, 2003

Related U.S. Application Data

(63) Continuation of application No. PCT/IE01/00039, filed on Mar. 23, 2001.

(30) Foreign Application Priority Data

Mar. 23, 2000 (IE) .......................................... 2000/0225
Jul. 11, 2000 (IE) .......................................... 2000/0559

(51) Int. Cl.[7] .................................................. A61B 1/00
(52) U.S. Cl. ........................ 600/114; 600/121; 600/125
(58) Field of Search ................................ 600/114, 115, 600/101, 121, 124, 125; 604/524, 526, 527

(56) References Cited

U.S. PATENT DOCUMENTS

| 5,168,863 | A | * | 12/1992 | Kurtzer ........................ 600/122 |
| 5,620,408 | A | * | 4/1997 | Vennes et al. ............... 600/114 |
| 5,733,241 | A | * | 3/1998 | King ............................ 600/114 |
| 5,779,624 | A | * | 7/1998 | Chang ......................... 600/114 |
| 5,941,815 | A | | 8/1999 | Chang |
| 6,116,741 | A | * | 9/2000 | Paschal ....................... 359/510 |

FOREIGN PATENT DOCUMENTS

| JP | 07-079909 | 3/1995 |
| JP | 10-155733 | 6/1998 |
| JP | 10-248794 | 9/1998 |

* cited by examiner

*Primary Examiner*—Beverly M. Flanagan
(74) *Attorney, Agent, or Firm*—Kudirka & Jobse, LLP

(57) ABSTRACT

An insertion device (82) to aid introduction of an overtube (90) into a colon over a previously inserted colonoscope (2). The insertion device (82) comprises an elongate tubular sheath (80), which defines a lumen to receive the colonoscope (2) and the overtube (90), a band (61) of resilient material to hold the sheath (80) to the colonoscope (2) during introduction of the colonoscope (2) with the insertion device (82) mounted thereto into a colon, and an inflatable holder (81) for gripping the sheath (80) to the colonoscope (2) during insertion of the overtube (90) into the sheath (80). The holder (81) is deflated to release the grip on the colonoscope (2) and the insertion device (82) is at least partially removed from the colon after the overtube (90) has been inserted into the colon.

29 Claims, 25 Drawing Sheets

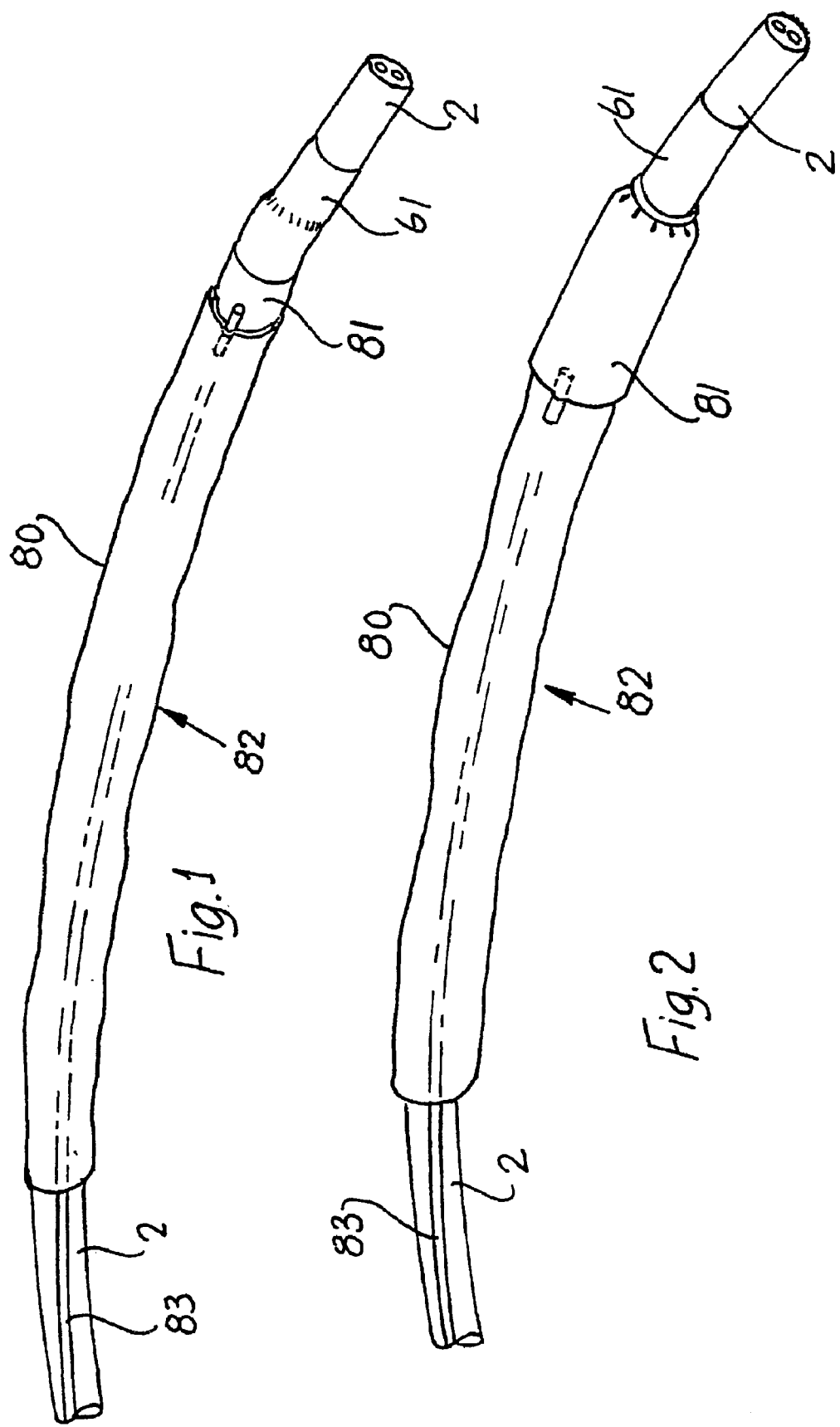

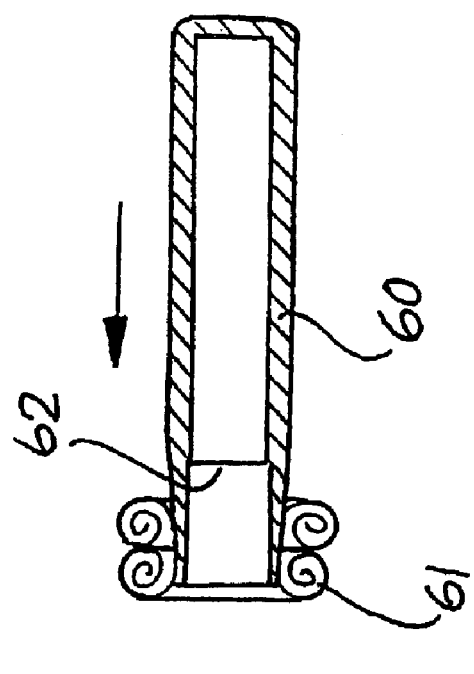
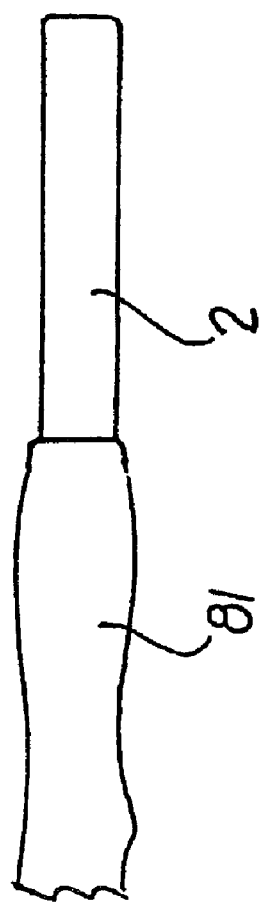
Fig. 4

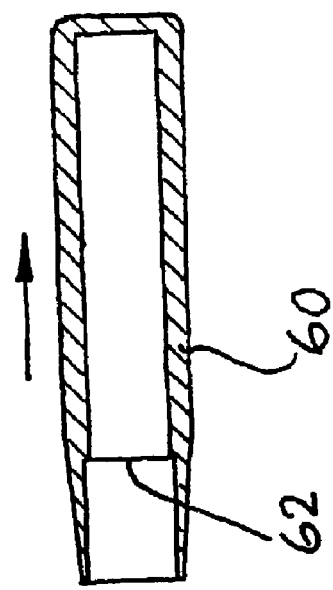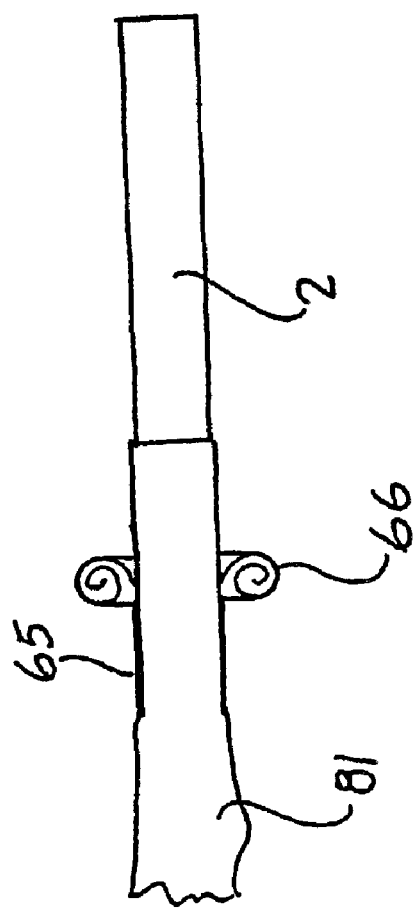
Fig. 8

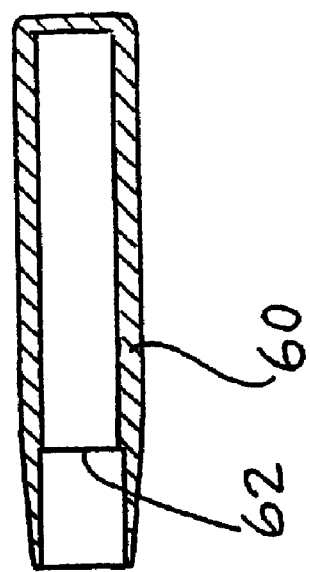
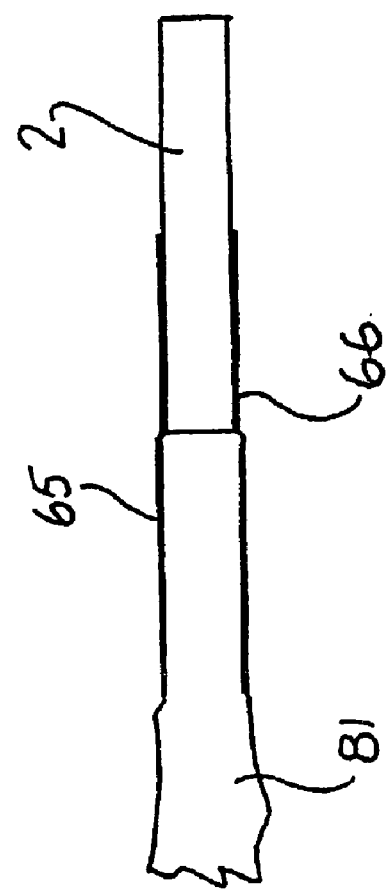
Fig. 9

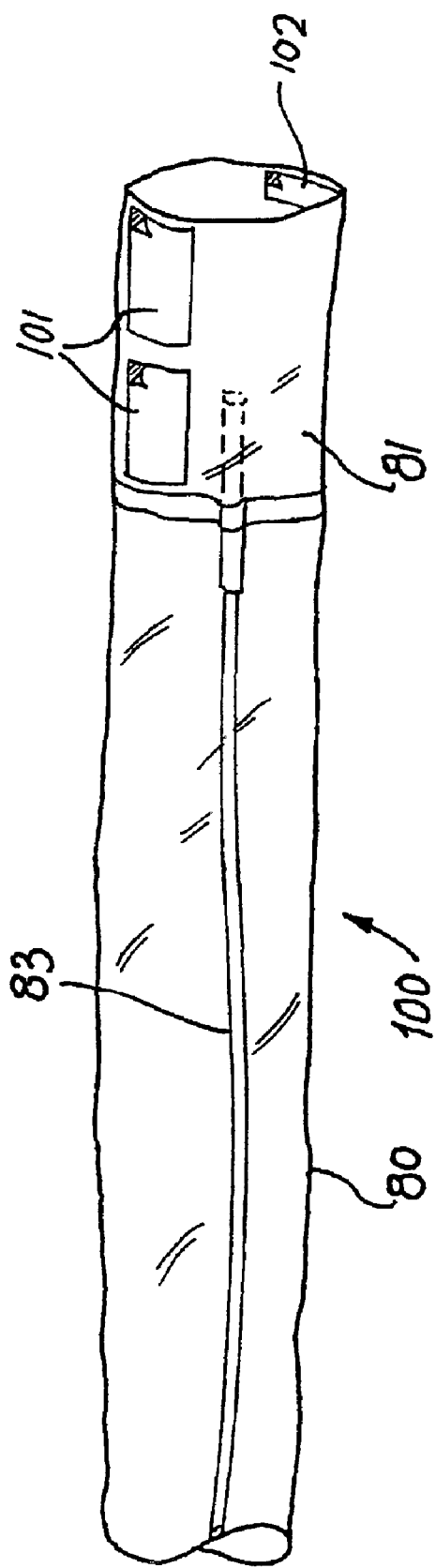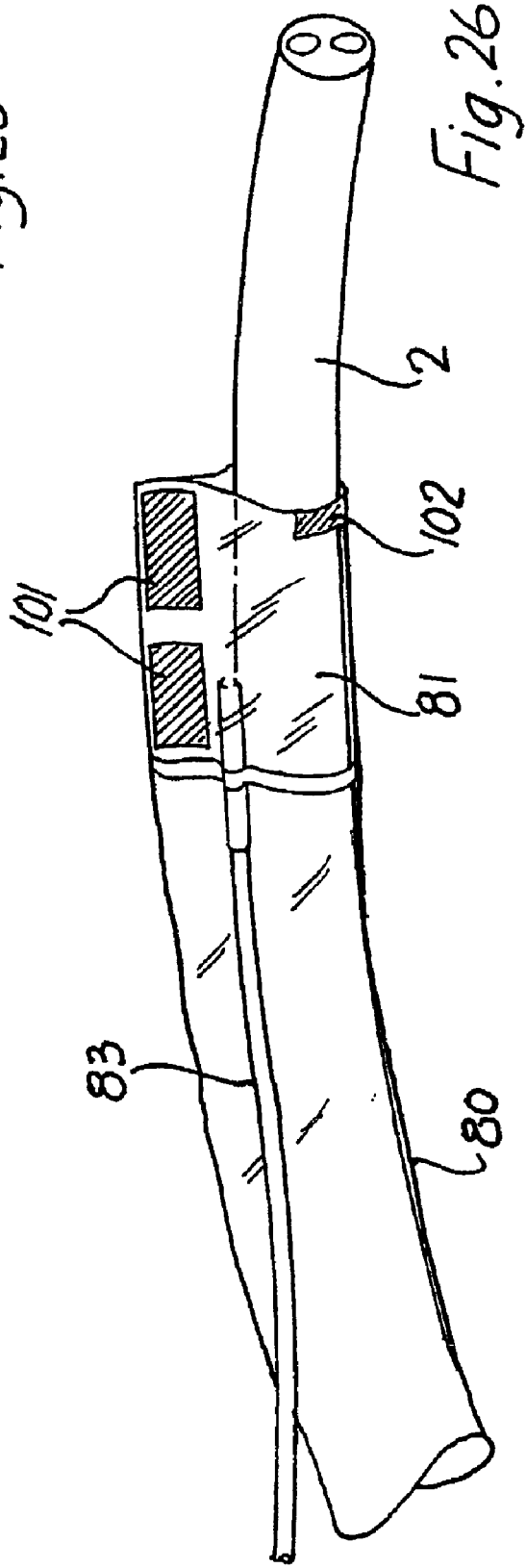

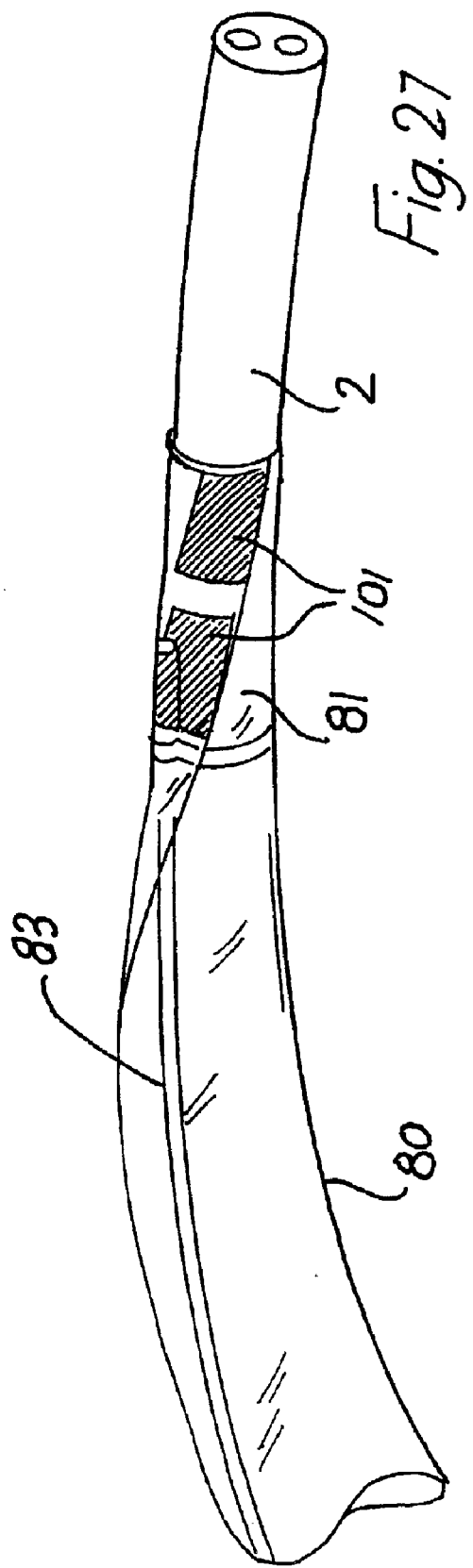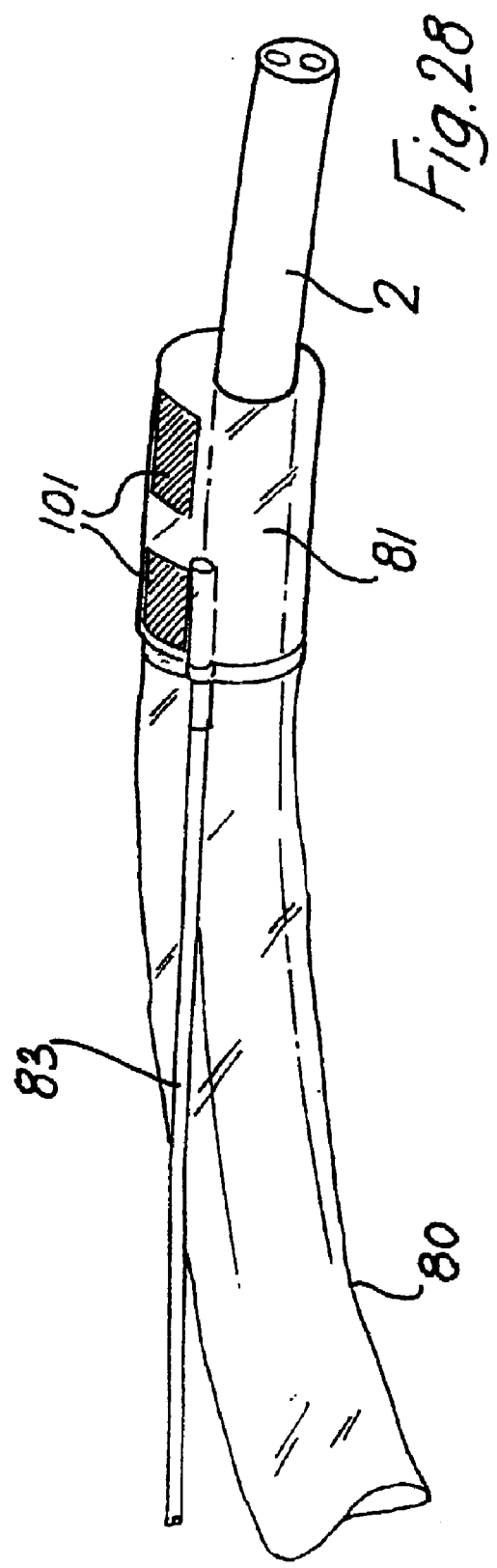

INSERTION DEVICE FOR AN ENDOSCOPE

CROSS REFERENCE TO RELATED APPLICATIONS

This application is a Continuation of PCT International Application No. PCT/IE01/00039, filed on Mar. 23, 2001.

INTRODUCTION

This invention relates to an insertion device to aid introduction of a probe and/or an overtube into a passageway, the overtube being used to assist in passage of the probe.

The term probe refers to any instrument for delivery to a site of interest, for example in a body cavity. The instrument may be for examination, diagnosis or treatment such as a visualisation device, especially an endoscope. The endoscope is preferably a medical endoscope such as a colonoscope, gastroscope, enteroscope or the like.

Modern colonoscopes consist of a control section attached to a long flexible shaft with a steerable tip. The flexible shaft carries several tubes for light, air, water and suction. Light is transmitted through non-coherent fibre-optic bundles and images are transmitted from a miniature CCD TV camera positioned on the tip of the colonoscope. In some cases a biopsy channel with a larger bore to allow therapeutic procedures to be performed is also provided.

A control mechanism is used to steer the colonoscope through the colon using control wheels at the proximal external end of the device. There are usually two wheels: one for lateral control and the other for vertical control. These control wheels are attached to guide wires that extend through and are attached to the tip of the colonoscope. The colonoscope is typically 100–150 centimetres long and must be pushed from the distal end and guided through tortuous passages using external manipulation. Applying torque to the colonoscope can also assist in advancing it past bends in the colon.

The lower gastrointestinal tract comprises the rectum and the large intestine or colon. The colon, in a textbook arrangement of its anatomy, extends upwards from the lower right quadrant, traverses the width of the body just below the diaphragm, travels downwards along the left side of the abdomen and then loops in an anterior retrograde manner before linking up with the rectum and the anus. Even in such a textbook arrangement, the large intestine is difficult to cannulate with a colonoscope due to the flexible nature of the shaft of the instrument and the floppy nature of the colon. This is even more difficult with the more realistic anatomies of actual people. In some people the sigmoid colon can be very long and is unfixed, except by its mesentery, and so can be extremely difficult to cannulate due to its predisposition to form loops when a colonoscope is pushed through it. Some anatomical landmarks, such as the recto-sigmoidal junction, the splenic flexure and the hepatic flexure, are also difficult to pass through simply because of their tortuous nature. Looping of the colonoscope within the sigmoid colon exacerbates the problems in traversing these areas.

Normally the act of inserting the colonoscope through the sigmoid colon causes it to stretch out the redundant sections of the colon. A loop often forms, the size of which is limited only by the degree to which the mesentery will stretch. The presence of this loop often reduces the ability of the endoscopist to proceed much further than to the descending colon. Attempts to pass through the splenic flexure will often simply cause the sigmoid loop to increase in size, stretch the mesentery and cause considerable pain and discomfort to the patient.

The sigmoid loop can sometimes be removed by making the redundant bowel contract into a shorter segment, like the bellows of an accordion or concertina, giving the walls of the sigmoid colon a corrugated appearance. This is accomplished by several techniques known to those skilled in the art of lower gastro-intestinal (GI) endoscopy. Unfortunately, further pushing of the colonoscope into the colon can cause the loop to re-form.

It is known to advance a stiff overtube over the inserted colonoscope after the sigmoid colon has been reduced to the accordioned configuration. The overtube then acts as a splint to maintain the sigmoid colon in the accordioned configuration during subsequent advancement of the colonoscope further into the colon.

Insertion of the overtube into the colon may however be a difficult task. In particular, the insertion of the overtube may cause loops in the sigmoid colon to re-form. In addition, advancement of the overtube through the colon may be a difficult and painful procedure due to frictional resistance at the colon walls.

One particular overtube proposed as a means of preventing the reformation of loops in the sigmoid colon consists of a semi-rigid plastic tube approximately 35–70 centimetres in length and 2–3 centimetres in diameter. The tube is slid over the colonoscope after the sigmoid colon has been reduced into a straightened accordioned configuration. In one embodiment of the device it is slit down its entire length and may be placed onto the colonoscope after the straightening manoeuvre. In another embodiment of the device it does not have a slit and so needs to be preloaded onto the colonoscope before the colonoscope is inserted into the colon. It is then referred to as a muzzle-loaded overtube.

The purpose of the stiffening overtube is to lend support to the reduced sigmoid colon and to isolate the walls of the colon from the colonoscope. This should prevent the reduced sigmoid colon from expanding and re-looping. By keeping the sigmoid colon straight it is easier to steer the colonoscope around the acute bends found at the splenic and hepatic flexures.

Several problems have been identified with stiffening overtubes causing them to lose favour very soon after they were introduced to the medical community. The slit overtube suffers from an inherent problem in that it is possible for sections of the colon wall to become entrapped between the sharp edges of the slit. This can happen if the overtube bends slightly, causing the slit to open and allow some colon into the slit. When the bend straightens the colon can be nipped by the slit as it closes. This problem can be worse if the overtube is moving at the same time. Other non-slit overtubes do not suffer from this particular problem. However all overtubes have the potential to damage the inner colon wall as they are inserted into the colon over the endoscope by entrapping the inner wall of the colon between the overtube's leading edge and the colonoscope.

In an attempt to prevent this from happening it is recommended that the overtube should only be slid over the colonoscope into the reduced sigmoid colon when it is significantly straight. However it is difficult to determine that the sigmoid colon is in a straight configuration without the use of some imaging or visualisation technology. One such method is by the use of fluoroscopy where an x-ray of the patient's abdomen may be taken and the colonoscope can be seen to be straight. However it will be necessary to take x-rays in more than one plane to be sure that the colonoscope, and therefore the sigmoid colon, is truly straight. Another method of determining the straightness of the sigmoid colon is by the use of magnetic sensing coils that can be placed into the biopsy channel of the colonoscope and the position of which can be determined in three-dimensional space by the use of field generating magnetic coils and appropriate computer analysis. While these solutions are feasible and have been used in the past it is clear that they are not very practical. It was the unwillingness to adopt such necessary practices for the safe introduction of the stiffening overtube that led to its failure as a feasible device for assisting with colonoscopy.

In view of these problems it is not surprising that colonoscopy is a difficult technique that can only be mastered after performing many hundreds of examinations. The ability to speedily cannulate the bowel and traverse the entire colon all the way to the caecum is a skill that is only enjoyed by a minority of endoscopists. Published research on the subject of difficulty encountered in colonoscopy shows that the procedure fails in up to 15% of cases where failure is defined as inability to reach or visualise the caecum. Up to 35% of cases are considered to be difficult as defined by extended duration of the procedure and experience of pain by the patient. Other research shows that up to 29% of cases are considered to be technically difficult.

There is therefore a need for an insertion device which will aid introduction of a probe and/or an overtube into a passageway. In particular there is a need for a device which will facilitate a colonoscopy to be performed more easily and more efficiently, especially without the need for expensive, cumbersome imaging equipment.

STATEMENTS OF INVENTION

According to the invention there is provided an insertion device to aid introduction of a probe and/or an overtube into a passageway, the device comprising an elongate tubular sheath for extending through a passageway, the sheath defining a lumen to receive a probe and/or an overtube, and a holder to hold the sheath to a probe and/or an overtube.

According to the invention there is also provided an insertion device to aid introduction of a probe and an overtube for the probe into a passageway, the device comprising an elongate tubular sheath for extending through a passageway, the sheath defining a lumen to receive a probe and an overtube for the probe, and a holder to hold a probe to the sheath on movement of the device through a passageway.

In one embodiment the sheath has a distal end and the holder is located at the distal end of the sheath.

In a preferred embodiment the holder comprises a first holder for holding the sheath to a probe on insertion of the probe into a passageway.

In another preferred embodiment the holder comprises a second holder for holding a probe to the sheath on insertion of an overtube into the sheath. Preferably the second holder is movable from a release configuration to a probe engaging configuration. Ideally the second holder is movable by inflation from the release configuration to the probe engaging configuration. Most preferably the second holder comprises an inflatable tube, the tube having an inflation port for inflation of the tube. The inflation port preferably has a connection means for connection to a supply of inflation fluid.

In one embodiment the tube is integral with the sheath.

In another embodiment the tube is attached to the sheath.

In another embodiment the first holder is movable from an engaged configuration in which the first holder grips the probe to a release configuration in which a probe is movable relative to the first holder. Preferably the first holder comprises an adhesive strip.

The fastener may comprise a strip of a hook-and-pile material.

The fastener may comprise a band of a resilient material.

In one embodiment the first holder comprises a drawstring. Ideally the drawstring is threaded back through the device and/or a probe received within the lumen to facilitate proximal manipulation thereof.

In another aspect the invention provides an apparatus for carrying out a procedure comprising a probe, an overtube, and a device of the invention to aid introduction of the overtube. In a particular embodiment the procedure is an endoscopy and the probe is an endoscope.

Preferably in an insertion configuration the device is mounted to the probe. Ideally the probe has a tip, and in the insertion configuration the tip extends distally of the device.

In one embodiment the device has a distal end, and in the insertion configuration the device is releasably secured to the probe adjacent its distal end.

In a preferred embodiment the overtube includes a stop to prevent complete insertion of the overtube. Ideally the stop is provided by a flange at a proximal end of the overtube.

In one embodiment the endoscope is a colonoscope.

In a further aspect the invention provides a method for carrying out an examination and/or a treatment and/or a diagnostic procedure comprising the steps of:

providing a probe, an overtube for the probe and an insertion device to aid introduction of the probe and/or the overtube;

mounting the insertion device to the probe;

introducing the probe with the insertion device mounted thereto into a passageway;

gripping the insertion device to the probe;

introducing the overtube into the passageway between the probe and the insertion device;

releasing the grip of the insertion device to the probe;

removing the insertion device, and the overtube, and the probe from the passageway.

In one embodiment the method comprises the step of holding the insertion device to the probe during introduction into a passageway. Preferably the method comprises the step of releasing the hold of the insertion device to the probe after introduction into a passageway and before gripping the insertion device to the probe. Ideally the hold is released by inflation of a portion of the insertion device.

In another embodiment the insertion device is gripped to the probe by inflation of a portion of the insertion device.

Desirably the method comprises the step of pulling the insertion device taut before introduction of the overtube between the probe and the insertion device.

In one embodiment the insertion device is at least partially removed from the passageway after releasing the grip of the insertion device to the probe, and before removal of the overtube and the probe from the passageway.

The probe preferably comprises an endoscope. Most preferably the endoscope comprises a colonoscope.

In a particularly preferred embodiment the colonoscope with the insertion device mounted thereto is introduced into a colon to the start of the descending colon before introduction of the overtube. Ideally the colonoscope is advanced through the descending colon after introduction of the overtube.

The sigmoid colon may be reduced to an accordioned configuration before introduction of the overtube.

The insertion device is preferably completely removed from the colon before advancing the colonoscope through the descending colon.

The insertion device according to the invention assists in the introduction of a probe and/or an overtube into a passageway. The device is particularly suitable to assist in the insertion of an overtube into a colon, the overtube in turn being used to assist in the passage of a colonoscope through the large intestine by preventing the formation of loops in the sigmoid colon. The device acts as a protective sheath to provide a substantially frictionless passage for the overtube through the sigmoid colon, and the device prevents loops from re-forming in the sigmoid colon.

The device consists of a polymeric sheath or skirt section approximately 72 centimetres long to which is attached at the distal end a double-layer polymeric inflatable sleeve. This is referred to as the clamp section. An inflatable tube leads proximally from the clamp section to facilitate inflation of the clamp section. The purpose of the clamp section is to firmly secure the device to the colonoscope while it is acting as a protective sheath for a stiffening overtube.

In use, the uninflated device is placed over the colonoscope and is positioned so that its leading or distal end is just behind the steerable tip. This is to prevent the device from interfering with the steering of the colonoscope. The device is typically 75 centimetres long but can be made in many other lengths. The device is releasably secured at the distal end of the colonoscope by a releasable clamp to prevent movement of the device relative to the colonoscope during insertion of the colonoscope into a colon.

The colonoscope with the device mounted on it in its uninflated state is inserted into the rectum as normal. The examination may then proceed in the normal manner. If a loop forms in the sigmoid colon it can be removed by contracting the redundant colon into an accordion or concertina configuration using known techniques.

When the distal end of the colonoscope is located within the descending colon and the sigmoid colon is in a straightened, accordioned configuration the device is ready to be deployed.

Deployment of the device is achieved by inflating the clamp section. This action causes the temporary fix mechanism to be released. The device is now secured to the colonoscope by the more secure inflatable clamp section.

In one embodiment of the device the temporary fix mechanism consists of strips of double-sided adhesive tape or some other disengagable material such as hook and pile material. In this embodiment the inflatable clamp is first secured to the distal end of the colonoscope with a strip of adhesive tape and another strip of adhesive tape is used to keep the inflatable damp snugly wrapped around the colonoscope.

In another embodiment, the device securement mechanism consists of a wide expandable band that covers the distal part of the device and extends from there onto the steerable tip of the colonoscope. In this manner the leading edge of the device is encapsulated by the securement mechanism and is sealed from the environment of the colon. This will prevent the influx of liquid or other material into the gap between the device and the colonoscope. The band is tight enough to hold the distal part of the device in position on the colonoscope. When the device is inflated the band rolls off the rounded distal end of the device towards the steerable tip of the colonoscope.

The band is preferentially placed into its encapsulating position on the device and the colonoscope using a specially designed sizing tool. This is a cylindrical tool that fits over the steerable tip of the colonoscope and extends down to the point at which the leading edge of the device should be positioned. The tool is employed by first placing the wide band onto it. This is achieved by rolling the wide band from each of its ends towards its centre and placing it onto the sizing tool. Then the steerable tip of the colonoscope in inserted into the sizing tool. The device is then slid up toward the colonoscope until its leading edge reaches the sizing tool. At this point the wide band is rolled onto the leading edge of the device and off the sizing tool. The sizing tool is removed and the distal end of the wide band is rolled towards the tip of the colonoscope thus encapsulating the leading edge of the device.

Once the clamp section has been inflated, the sheath section can be put under tension by pulling on it. This facilitates introduction of the overtube which is manually advanced over the scope and within the sheath section until the distal end of the overtube abuts the proximal end of the clamp section. Because the overtube has been isolated from the inner colon wall, it is impossible for the colon to become trapped between the colonoscope and the leading edge of the overtube.

When the leading edge of the overtube has reached the descending colon, the clamp section is deflated, causing it to release from the scope. Gentle tugging on the proximal end of the sheath causes the distal end of the clamp to be withdrawn over the distal end of the overtube where it will not interfere with the remaining part of the colonoscopy.

The colonoscopy examination can now continue more easily as the overtube holds the floppy sigmoid colon in its straightened accordioned configuration.

BRIEF DESCRIPTION OF THE DRAWINGS

The invention will be more clearly understood from the following description of some embodiments thereof, given by way of example only, with reference to the accompanying drawings, in which:

FIGS. 1 to 3 are perspective views of an insertion device according to the invention mounted to a colonoscope;

FIG. 4 is an enlarged, side, partially cross sectional view of the device and colonoscope of FIGS. 1 to 3 with an associated band applicator;

FIGS. 5 to 9 are views similar to FIG. 4 illustrating application of a band to the device and colonoscope of FIGS. 1 to 3;

FIG. 25 is a perspective view of another insertion device according to the invention; and FIGS. 26 to 28 are perspective views of the device of FIG. 25 mounted to a colonoscope.

DETAILED DESCRIPTION

Figure 3:
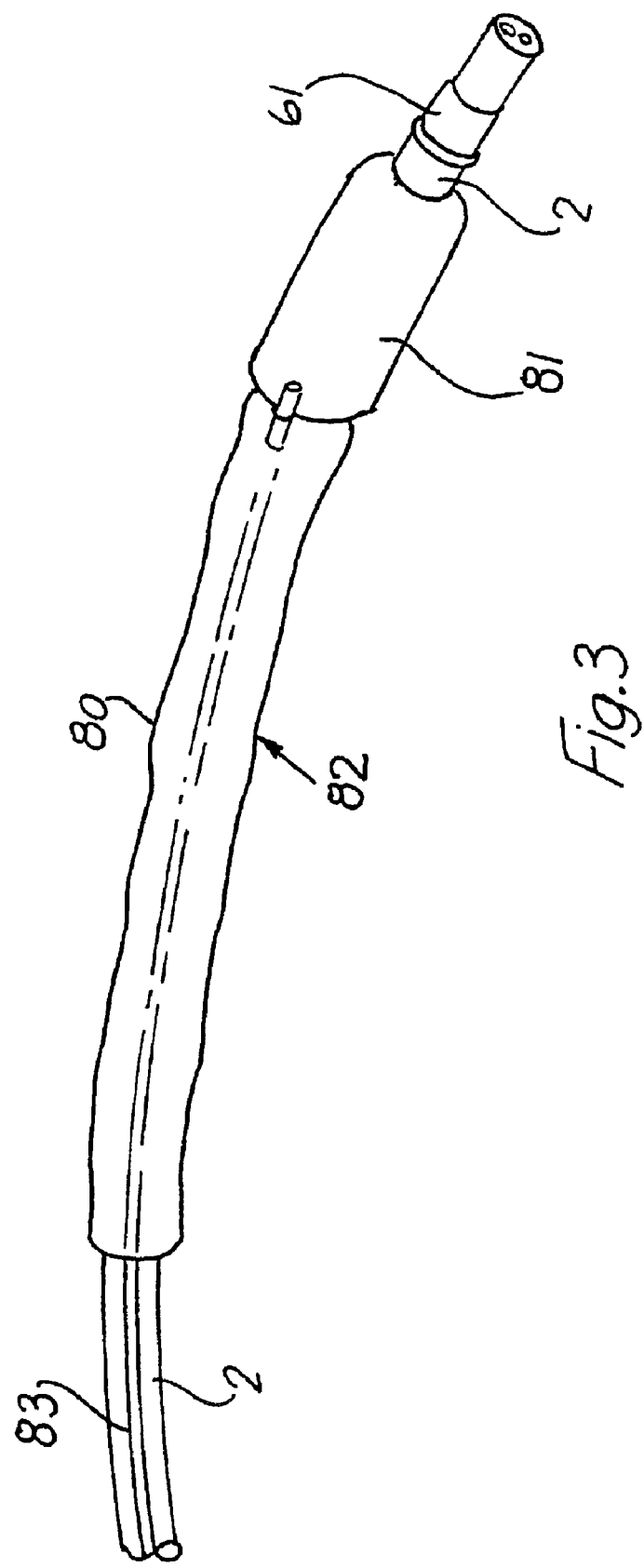

Referring to the drawings there is illustrated an insertion device according to the invention to aid introduction of a probe and/or an overtube into a passageway.

Referring initially to FIGS. 1 to 24 there is illustrated an insertion device 82 according to the invention for aiding introduction of an overtube, the overtube in this case being used during a colonoscopy procedure. FIGS. 1 to 3 illustrate the device 82 mounted over a colonoscope 2. The device 82 comprises an elongate tubular sheath 80 for extending through a passageway, such as a colon in this case, with a holder to releasably hold the sheath 80 to the colonoscope 2. The holder comprises a distal fixation mechanism for holding the sheath 80 to the colonoscope 2 during insertion of the sheath 80 through a passageway, such as a colon, and an inflatable tubular clamp section 81 to hold the sheath 80 to the colonoscope 2 during insertion of an overtube into the sheath 80.

During insertion and withdrawal of the device 82 from a colon, the clamp section 81 is in an uninflated configuration. The clamp section 81 is inflatable to grip the colonoscope 2. In this case the clamp section 81 is attached to a distal end of the sheath 80, however it will be appreciated that the clamp section 81 may alternatively be provided integral with the sheath 80. The clamp section 81 is preferably short relative to the tubular sheath 80. An inflation port 83 is provided extending proximally of the sheath 80 and in communication with the clamp section 81.

The uninflated clamp section 81 is held to the colonoscope 2 during insertion into a colon by the distal fixation mechanism, the fixation mechanism being provided, in this case, by a band 61 of resilient material encapsulating a distal end of the device 82 and the colonoscope 2 (FIG. 1). The band 61 is movable from an engaged configuration in which the band 61 grips the colonoscope 2 to a release configuration in which the colonoscope 2 is movable relative to the band 61. Upon inflation of the clamp section 81, a proximal part of the band 61 rolls distally towards the tip of the colonoscope 2 (FIG. 2). When the clamp section 81 is fully inflated the band 61 rolls off the end of the clamp section 81 (FIG. 3). The clamp section 81 is thereby released and the colonoscope 2 is then free to move relative to the band 61.

Referring now to FIGS. 4 to 10, the wide elasticated band 61, and the mounting of the band 61 to the device 82 and the colonoscope 2 is shown in more detail. The wide elasticated band 61 is placed into its encapsulating position on the device 82 and the colonoscope 2 using a band applicator 60. The wide elasticated band 61 is rolled from each of its ends towards its centre and placed onto the band applicator 60. The band applicator 60 is a cylindrical tool that fits over the steerable tip of the colonoscope 2 and extends back to the point at which the distal end of the device 82 should be positioned.

Figure 5:
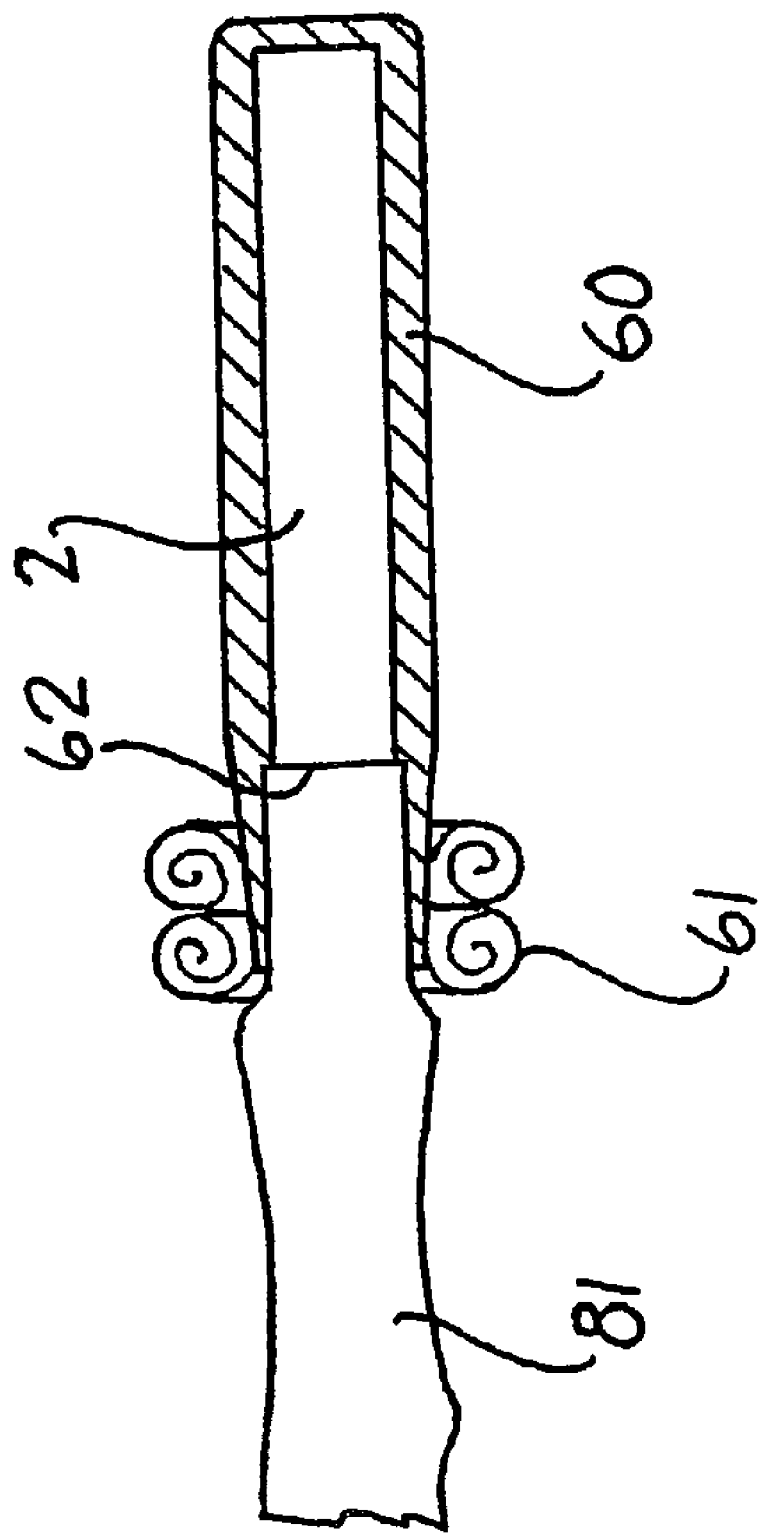

FIG. 4 illustrates the uninflated device 82 mounted on the colonoscope 2 with the distal tip of the colonoscope 2 extending from the distal end of the device 82. The band applicator 60 is shown with the rolled-up wide elasticated band 61 mounted on it. The band applicator 60 has a step 62 to locate the device 82 in a desired position. The colonoscope 2 is inserted into the band applicator 60 until it can go no further. The device 82 is then slid up to the positioning step 62 inside the band applicator 60 so that it assumes a correct distance from the tip of the colonoscope 2 (FIG. 5).

Figure 6:
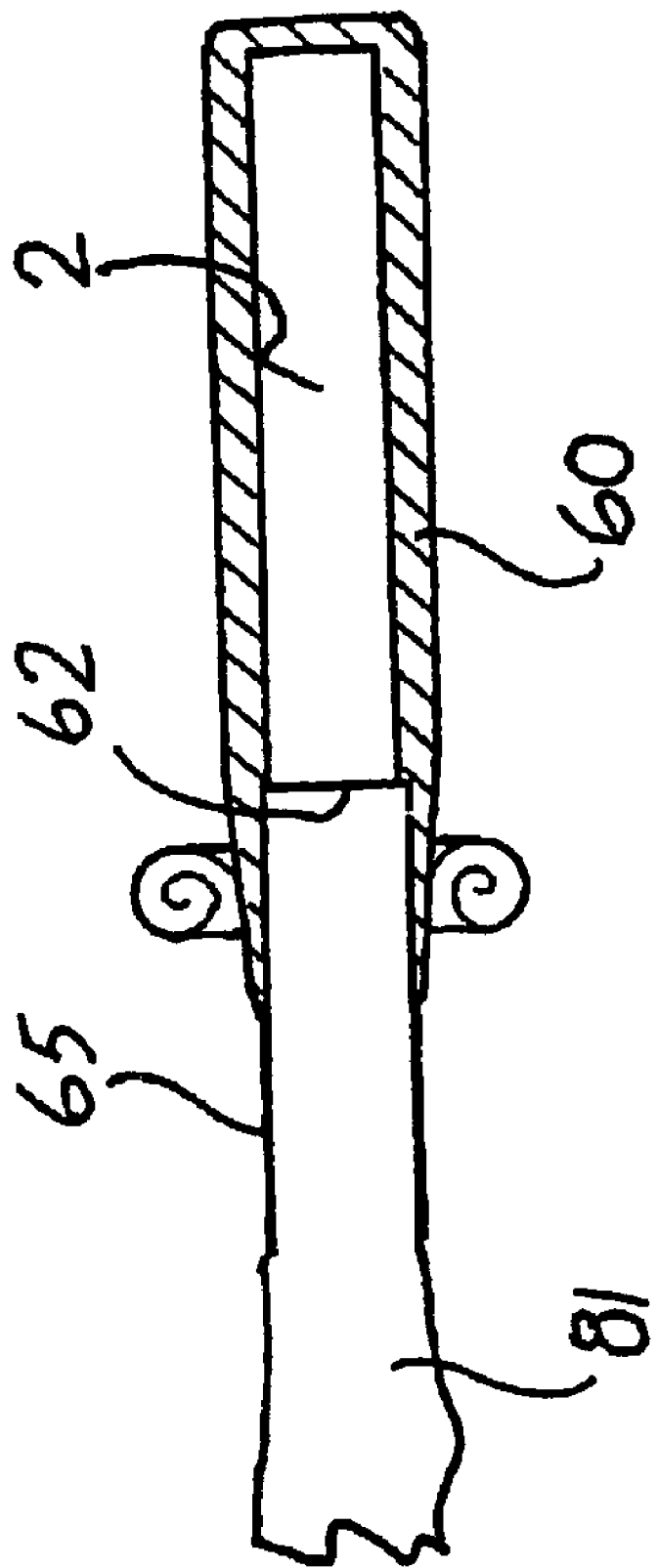
Figure 7:
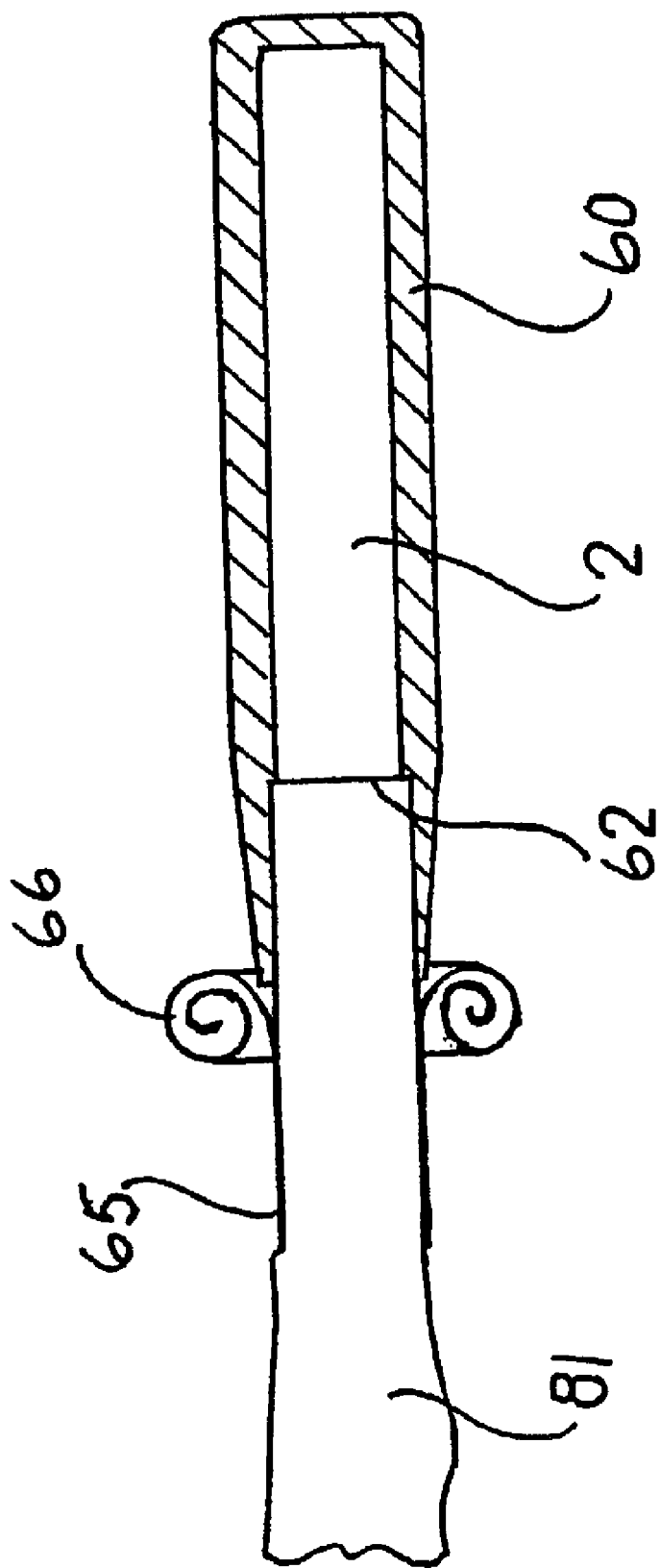

A proximal part 65 of the elasticated band 61 is rolled proximally onto the uninflated clamp section 81 (FIG. 6). A distal part 66 of the wide elasticated band 61 is then rolled proximally onto the uninflated clamp section 81 so that the band is no longer situated on the band applicator 60 (FIG. 7). The tip of the colonoscope 2 is then removed from the band applicator 60 (FIG. 8). The distal part 66 of the wide elasticated band 61 is rolled distally towards the tip of the colonoscope 2, thus encapsulating the distal end of the device 82 (FIG. 9).

Figure 10:
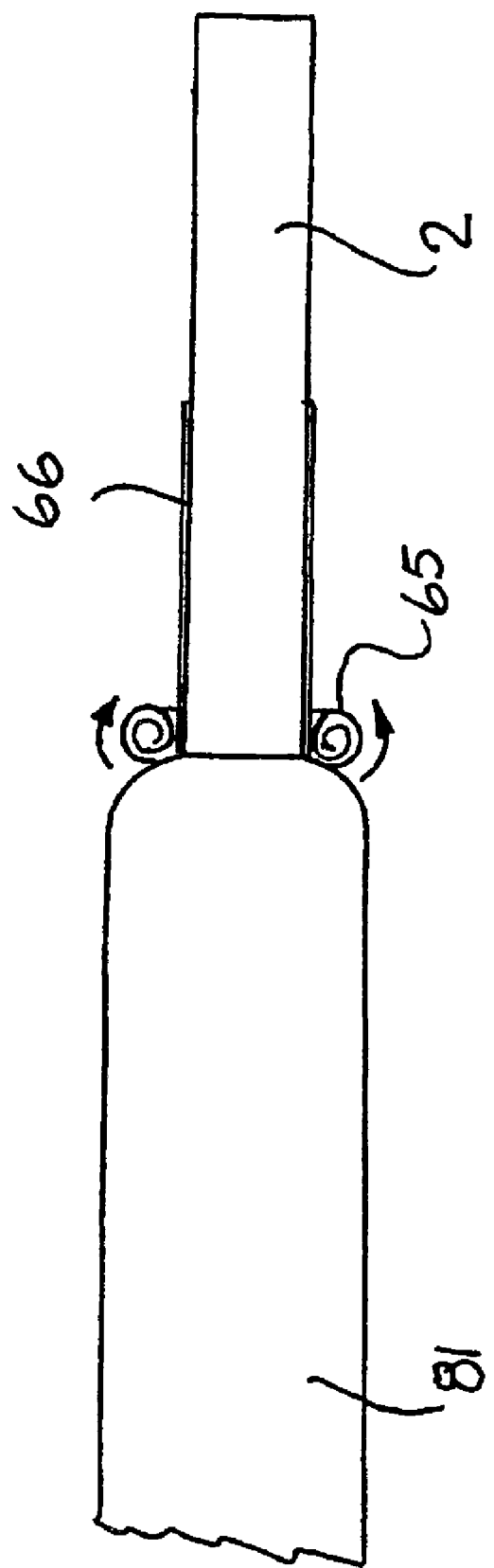
FIG. 10 is a view similar to FIGS. 4 to 9 illustrating release of the band.

The clamp section 81 of the device 82 may subsequently be inflated to cause the proximal part 65 of the wide elasticated band 61 to roll distally off the device 82 towards the tip of the colonoscope 2 (FIG. 10). The device 82 is then free to move relative to the colonoscope 2.

Figure 11:
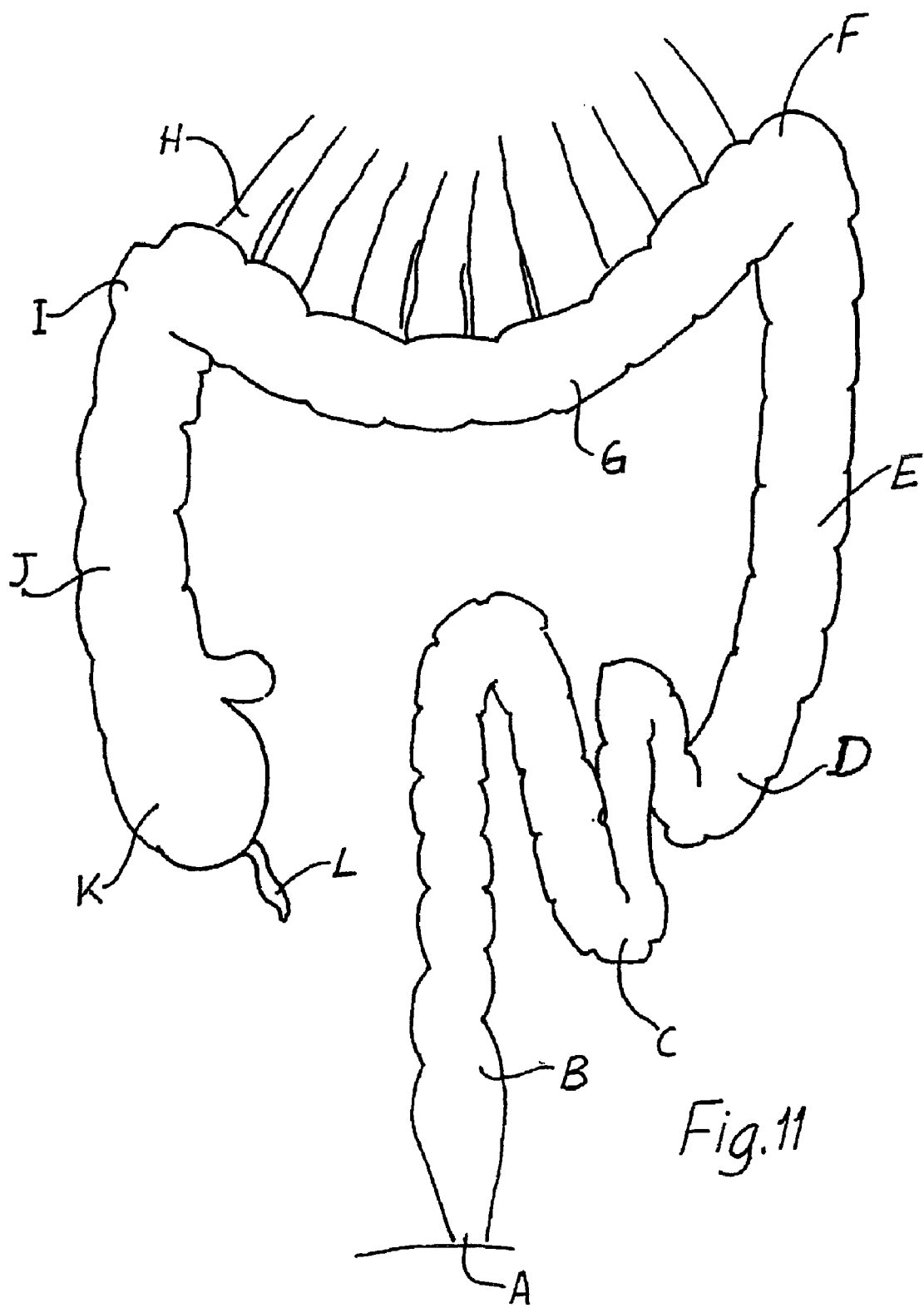
FIG. 11 is a schematic illustration of the major components of a large intestine, rectum and anus.

Referring now to FIGS. 11 to 24 there is illustrated the use of the device 82 in a colonoscopy procedure. FIG. 11 illustrates the major components of a large intestine, rectum and anus. The anus A leads into the rectum B which in turns leads into the sigmoid colon C having a mesentery N. From the sigmoid colon C a start D leads to the descending colon E which leads to the transverse colon G. The transverse colon G is attached to mesentery H and leads into the ascending colon J, which terminates in the caecum K, to which the appendix L is attached. Two relatively acute bends exist between the transverse colon G and the descending E and ascending J sections and are referred to as the splenic F and hepatic I flexures respectively.

The ascending and descending sections of the colon J, E are generally fixed in position while the transverse and sigmoid portions G, C are partially mobile, being attached to mesenteries H and N. The redundancy in the sigmoid colon C can also be seen.

Figure 12:
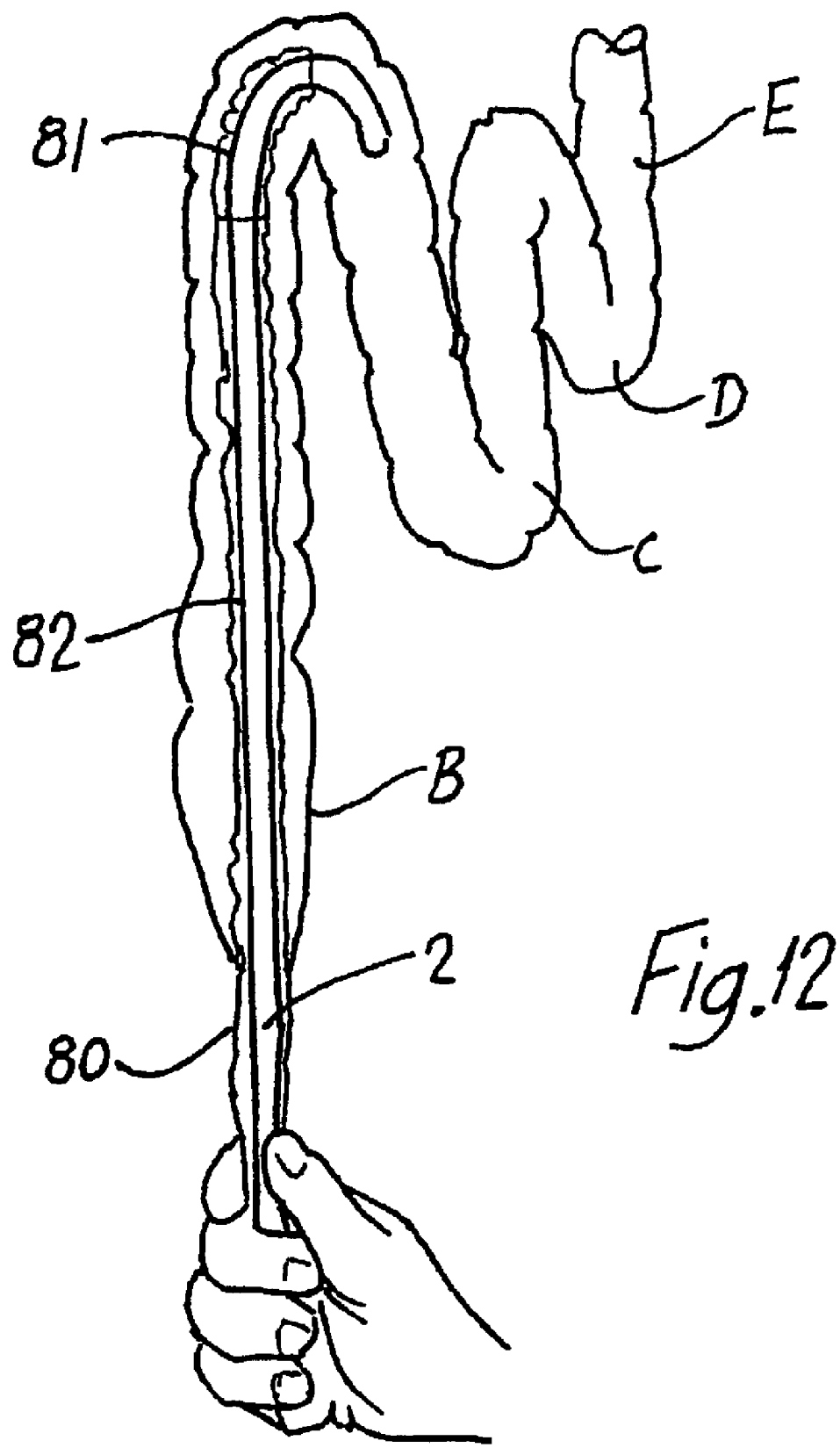
FIG. 12 is a front view of the device and colonoscope of FIGS. 1 to 10, partially inserted and uninflated.
Figure 13:
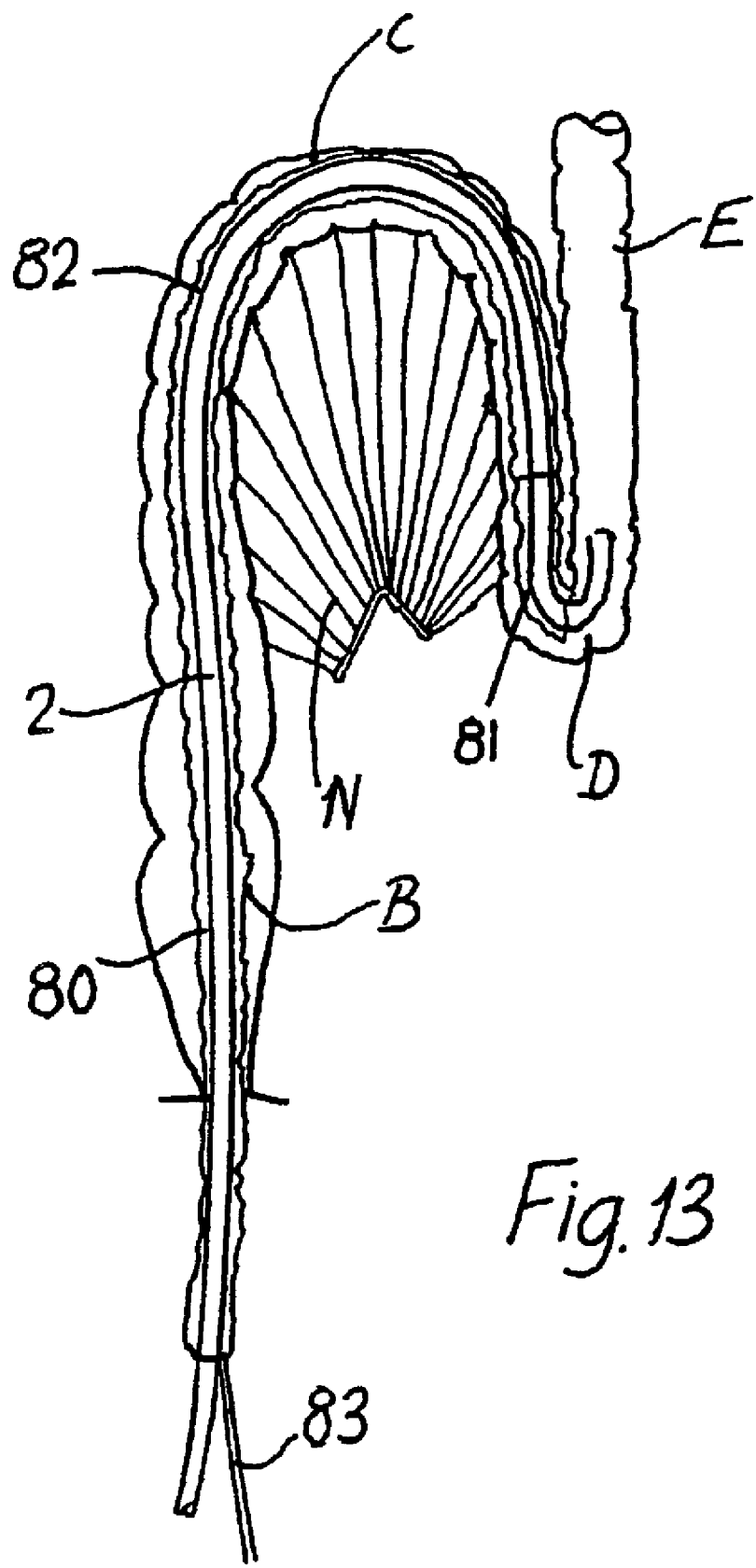
FIG. 13 is a front view of the device and colonoscope of FIGS. 1 to 10 inserted through the entirety of the sigmoid colon.
Figure 14:
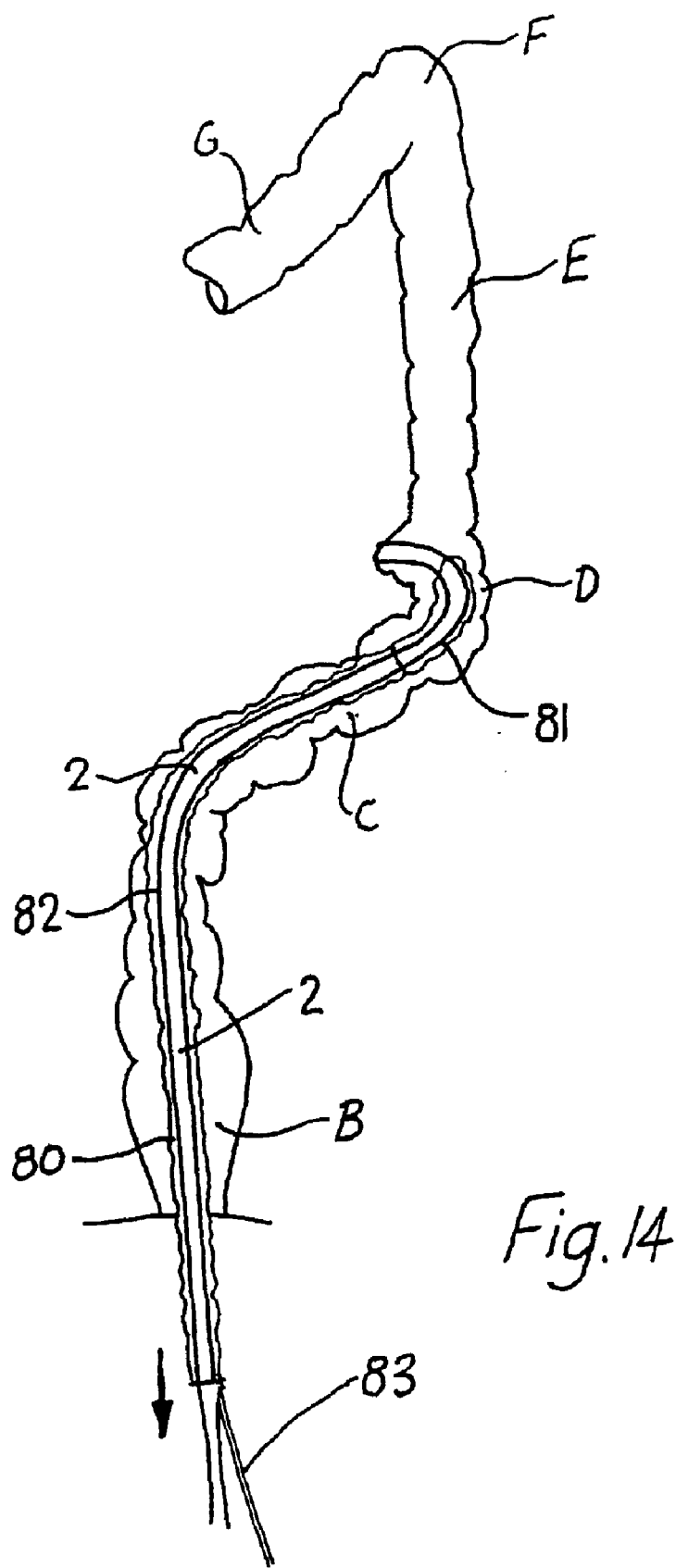
FIGS. 14 and 15 are front views illustrating the reduction of the sigmoid colon to an accordioned configuration.

In use, the device 82 is mounted to the colonoscope 2 in the uninflated configuration with the band 61 securing the uninflated clamp section 81 to the colonoscope 2, and the colonoscope 2 is partially inserted through the anus A and into the sigmoid colon C (FIG. 12). The device 82 is inserted through the entirety of the sigmoid colon C until the tip of the colonoscope 2 is at the proximal margin of the descending colon E (FIG. 13). The sigmoid colon C forms a loop during this advancement, the size of which is limited by the extent to which the sigmoid mesentery N will stretch.

Figure 15:
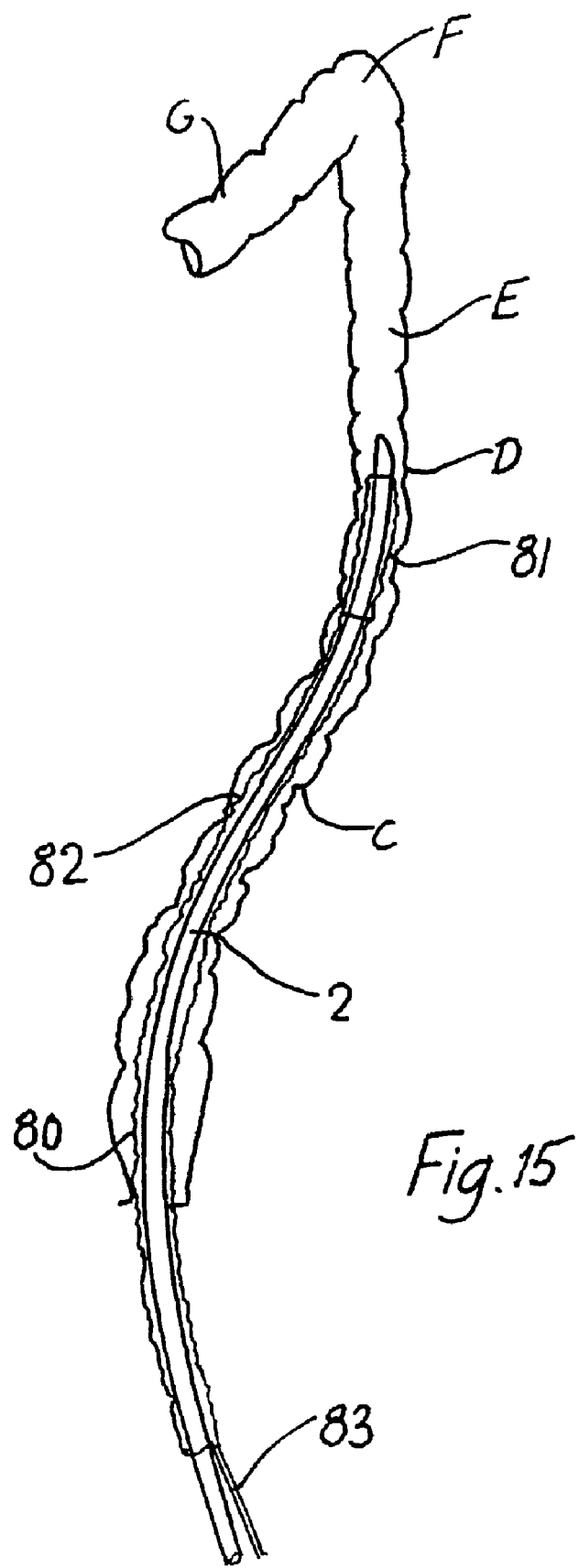

The sigmoid colon C is then reduced to an accordioned configuration by manoeuvres described above and known to those skilled in the art (FIG. 14). FIG. 15 illustrates the reduced, accordioned sigmoid colon C following the reduction manoeuvre.

Figure 16:
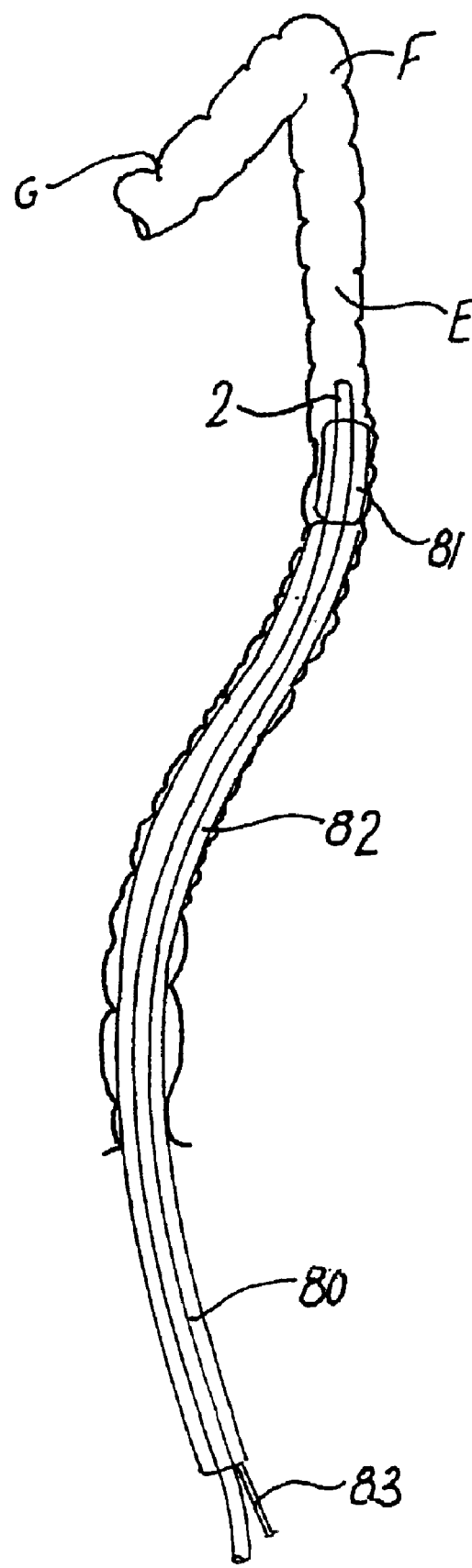
FIG. 16 is a front view after inflation of the device of FIGS. 12 to 15.
Figure 17:
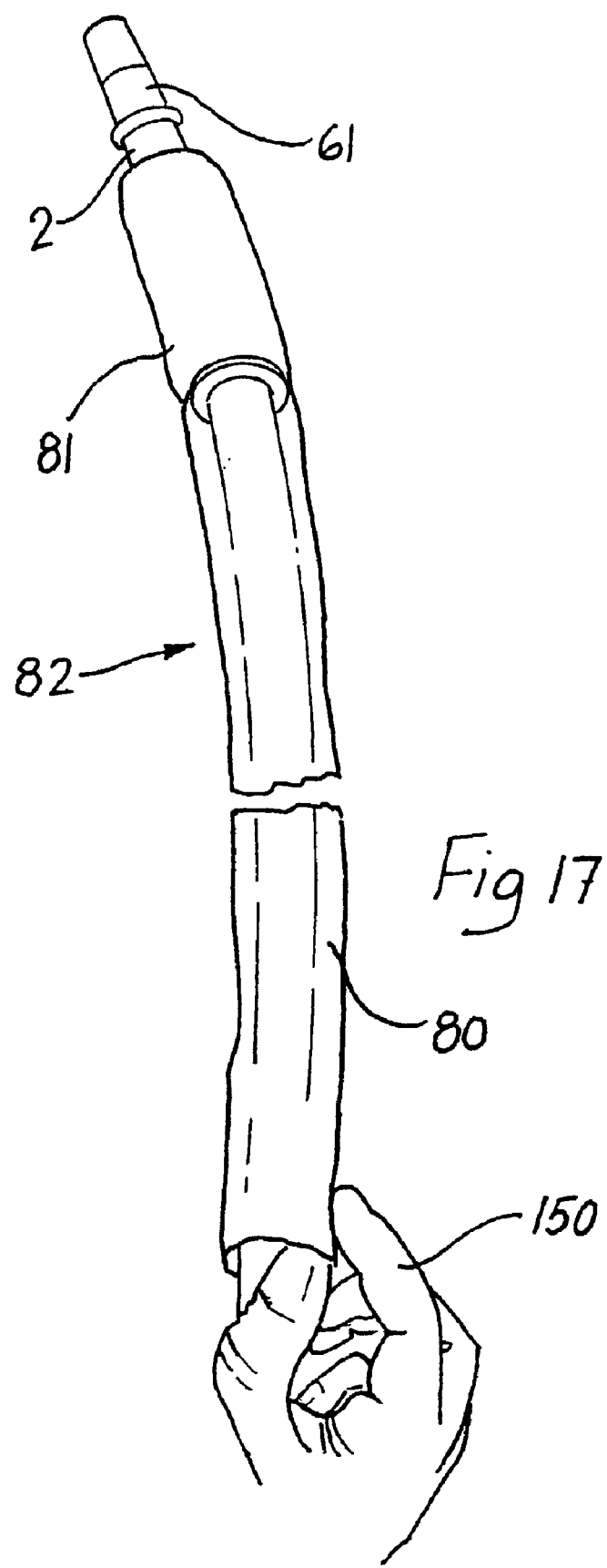
FIG. 17 is a perspective view of the device and colonoscope of FIG. 16 in use.
Figure 18:
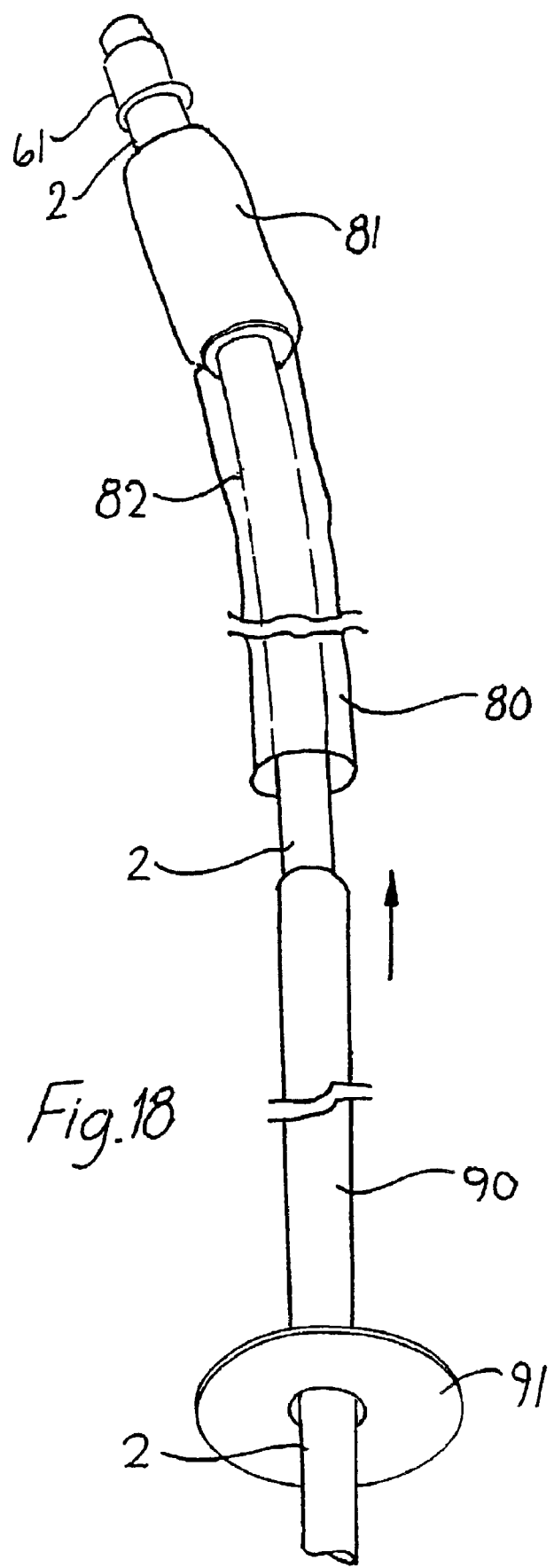
FIG. 18 is a perspective view of the device and colonoscope of FIG. 17 and an overtube.
Figure 19:
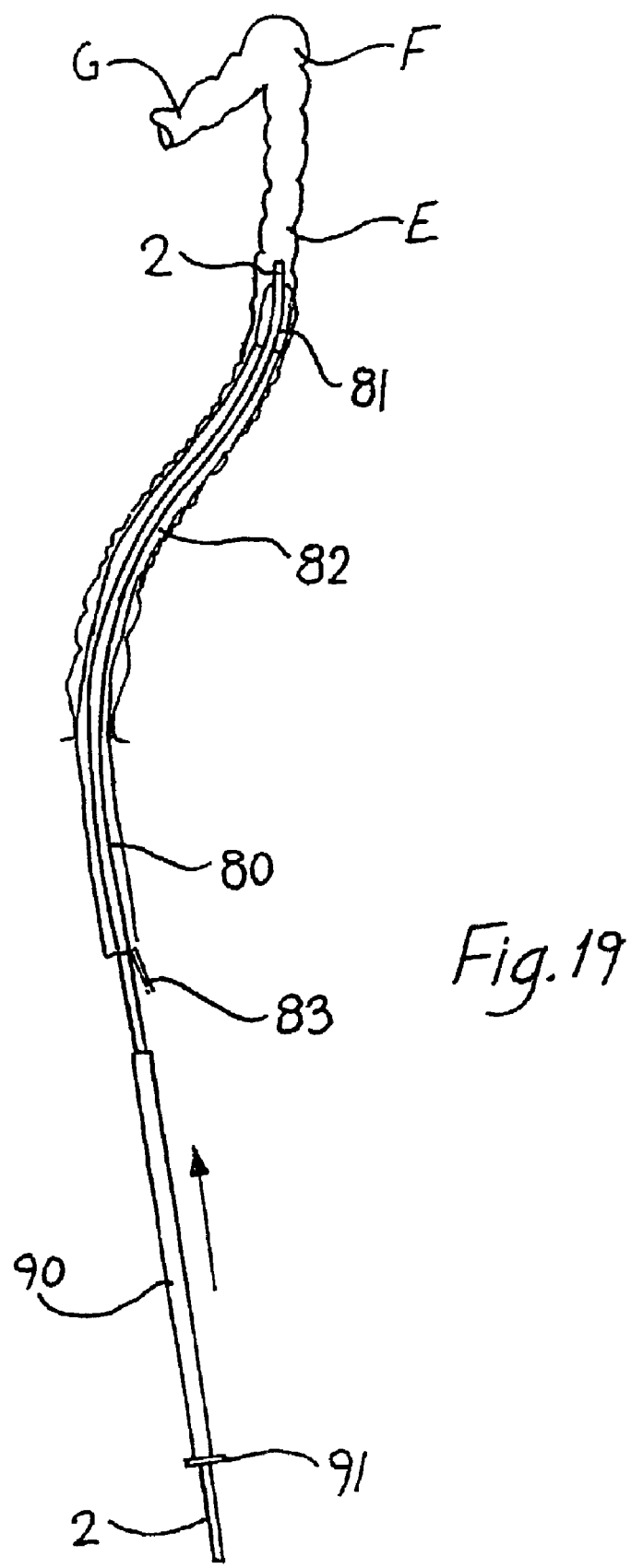
FIGS. 19 to 24 are front views of the device, colonoscope and overtube of FIG. 18 in use.
Figure 20:
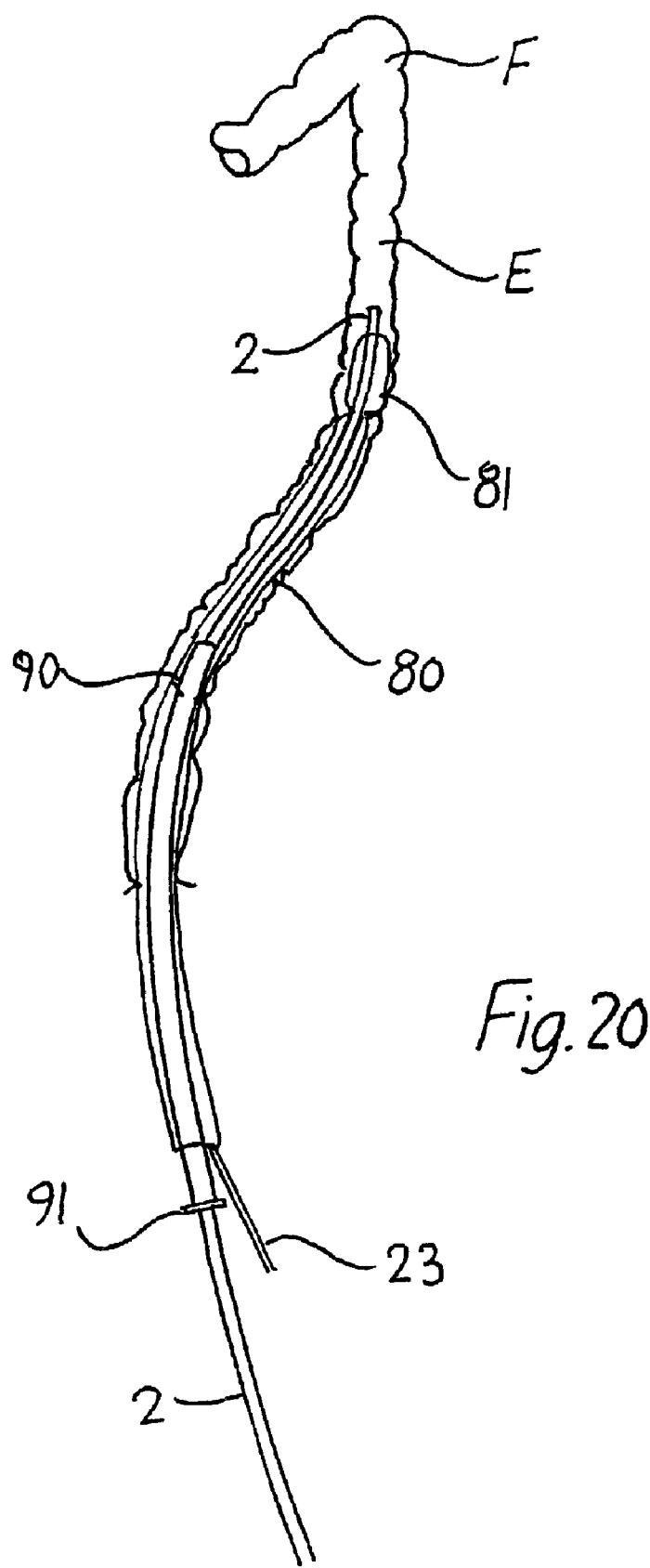
Figure 21:
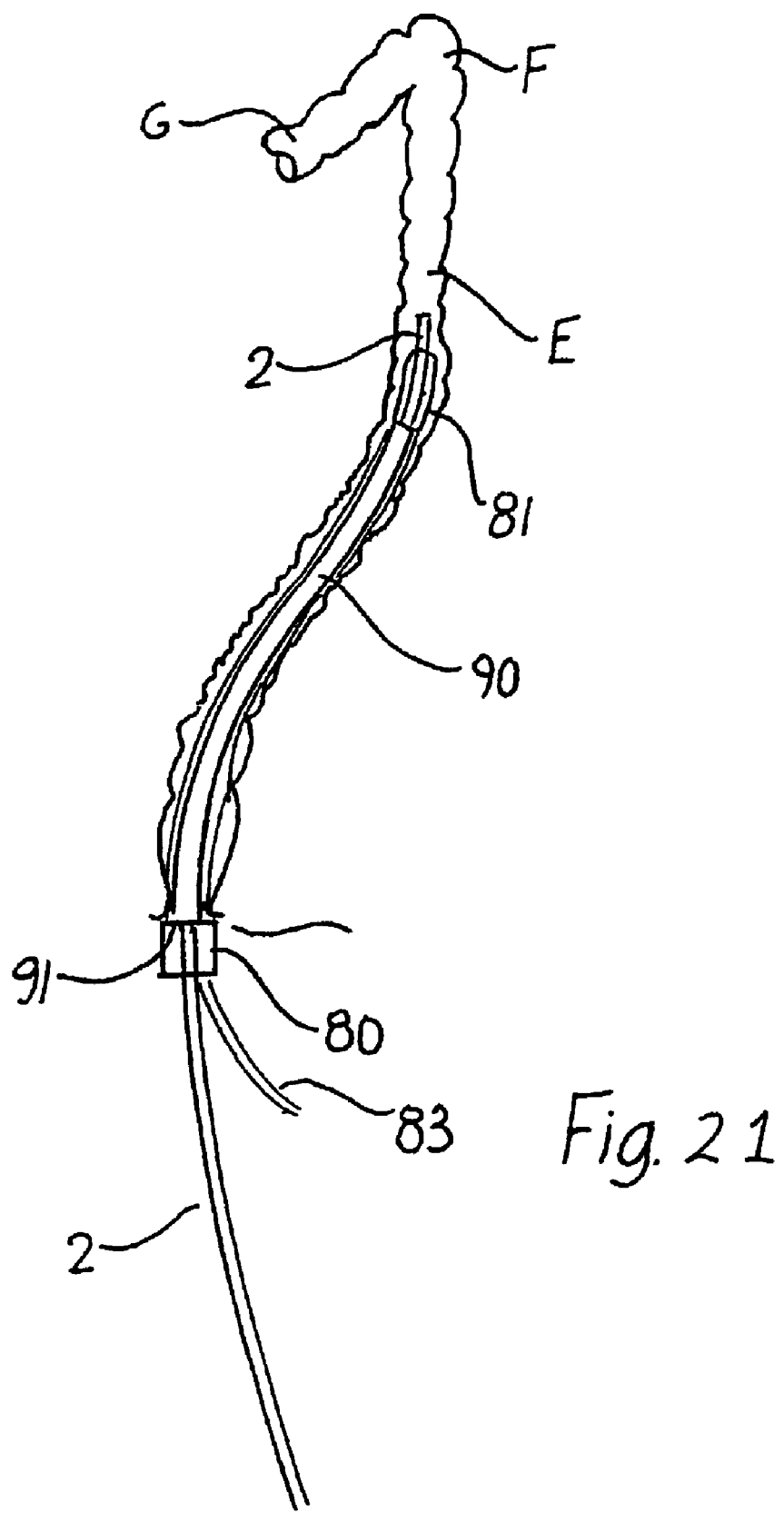
Figure 22:
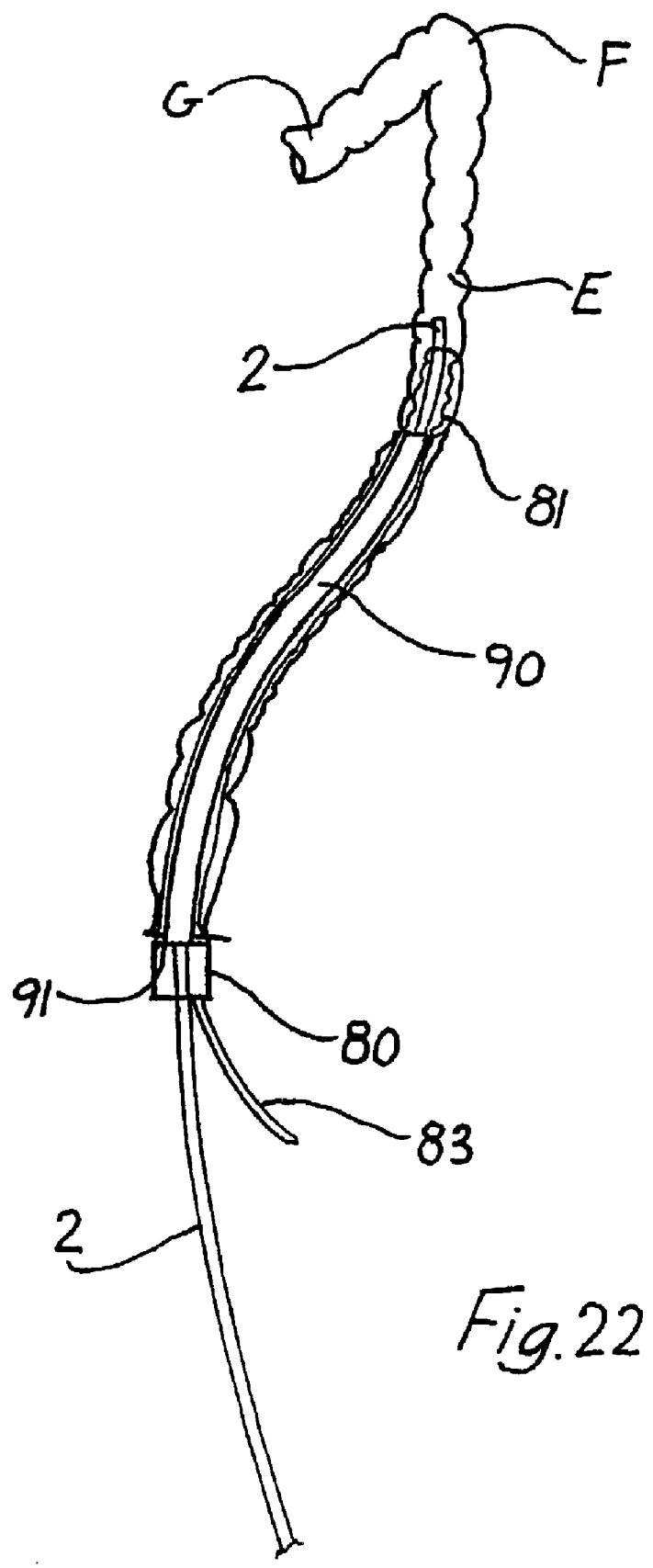

The clamp section 81 is then inflated securing the clamp section 81 to the colonoscope 2 and releasing the wide elasticated band 61 (FIG. 16). To advance the colonoscope 2 further into the descending colon E through the splenic flexure F and into the transverse colon G a stiffening overtube 90 is used. The overtube 90 has a detachable annular flange 91 at its proximal end which acts as a stop, and the internal bore through the overtube 90 is sized to enable the overtube 90 to be advanced over the colonoscope 2, as illustrated in FIG. 18. Alternatively the overtube may be sized such that its length will prevent it from complete insertion into the anus. By manually pulling the sheath 80 taut from a point external of the colon, easier passage of the overtube 90 over the colonoscope 2 and into the device 82 is achieved, as illustrated in FIG. 17. The inflated clamp section 81 firmly grips the colonoscope 2, thereby preventing the entire device 82 being pulled proximally over the colonoscope 2 and out of the colon as a clinician 150 pulls the sheath 80 taut.

Figure 23:
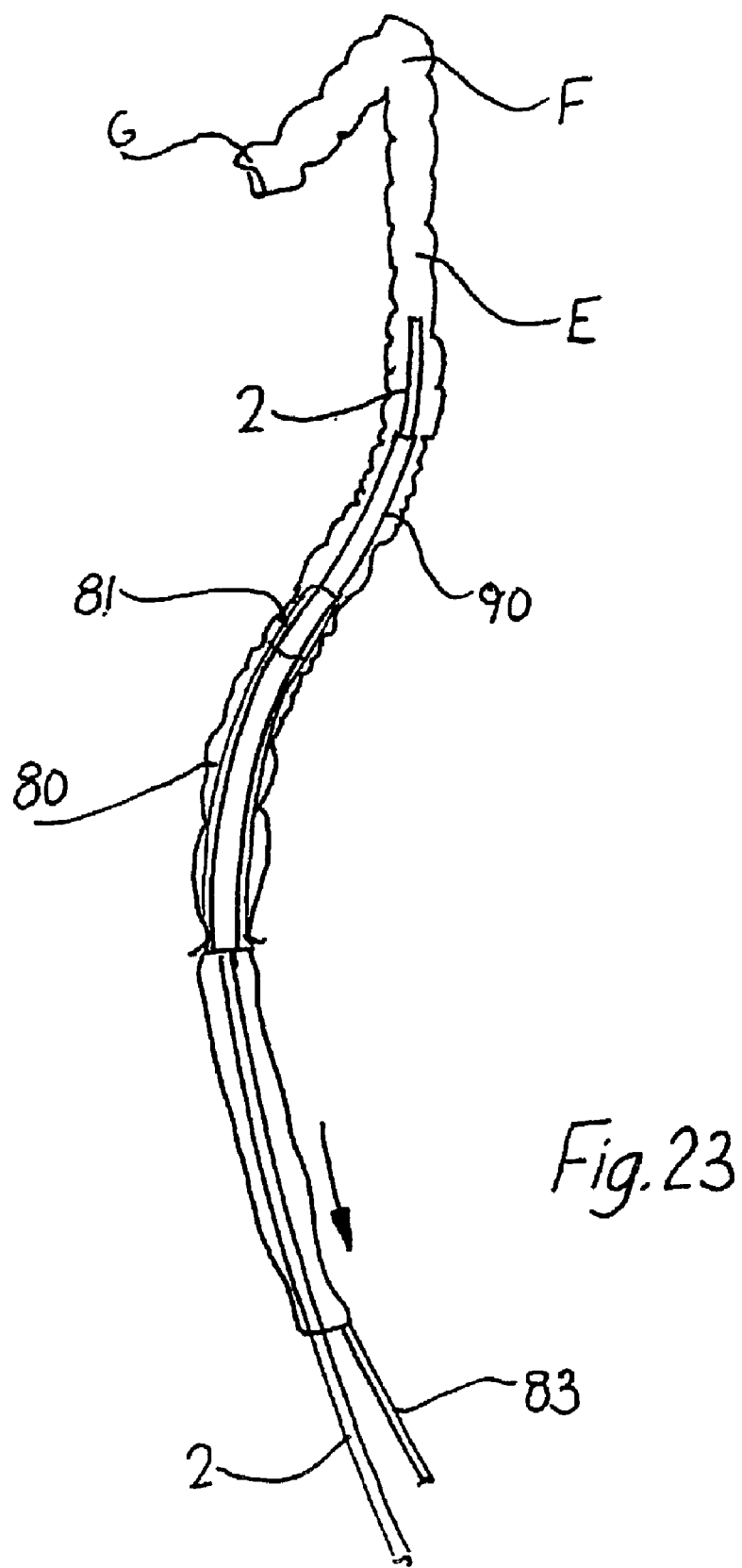

The overtube 90 is advanced over the colonoscope 2 (FIG. 19), into the sheath 80 of the device 82 (FIG. 20), until the flange 91 rests externally against the anus A (FIG. 21), while maintaining the sheath 80 taut. The flange 91 prevents complete insertion of the overtube 90 into the anus A. The clamp section 81 is then deflated through the inflation port 83 so that it no longer grips the colonoscope 2 (FIG. 22), and the device 82 is retracted proximally over the overtube 90 and the colonoscope 2 (FIG. 23). The device 82 may be retracted partially from the colon at his stage, or alternatively the device 82 may be completely withdrawn from the colon at this stage.

When the device 82 has been retracted, the colonoscope 2 is advanced distally into the descending colon E through the splenic flexure F and into the transverse colon G. When the colonoscopy procedure is complete the overtube 90 and the colonoscope 2 are removed from the colon.

Figure 24:
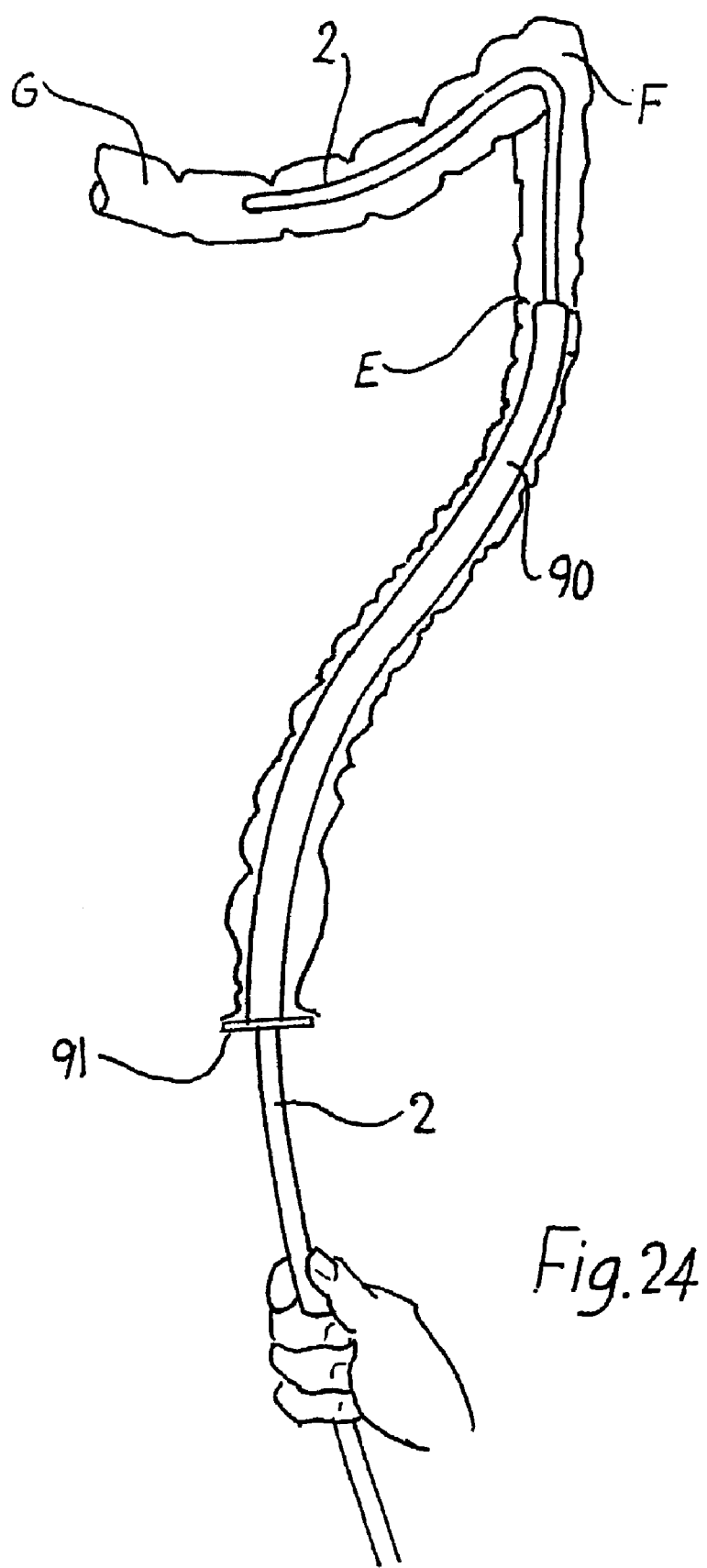

As illustrated in FIG. 24 the overtube 90 engages the inner wall of the sigmoid colon C, and the passage of the colonoscope 2 through the splenic flexure F is thus eased. The overtube 90 acts as a splint and maintains the sigmoid colon C in the reduced, accordioned configuration. The flange 91 prevents the complete insertion of the overtube 90 into the anus A as the colonoscope 2 is pushed through the overtube 90.

Referring to FIGS. 25 to 28 there is illustrated another insertion device 100 according to the invention which is similar to the insertion device 82 of FIGS. 1 to 24, and the same reference numerals are assigned to similar elements in FIGS. 25 to 28.

In this case, the distal fixation mechanism is provided by a plurality of double-sided adhesive strips 101, 102. One strip 102 is provided on the inner wall of the clamp section 81, and two strips 101 are provided on the outer wall of the clamp section 81, as illustrated in FIG. 25.

To hold the clamp section 81 to the colonoscope 2 before insertion into a colon, the backing is removed from the strips 101, 102, and the colonoscope 2 is inserted through the device 100 until the steerable tip of the colonoscope 2 protrudes distally of the clamp section 811 as illustrated in FIG. 26.

The inflated clamp section 81 is then wrapped tightly around the colonoscope (FIG. 27) to adhesively fix the strip 102 to the colonoscope 2, and to adhesively fix the two strips 101 to the clamp section 81. The strip 102 prevents the device 100 slipping proximally relative to the colonoscope 2 during insertion into the colon. In addition the strips 101 ensure that the clamp section 81 remains wrapped around the colonoscope 2 in a low-profile configuration during insertion.

The colonoscope 2 with the device 100 mounted thereto is inserted into the colon in a manner similar to that described previously with reference to FIGS. 12 to 15. Upon inflation of the damp section 81, the inflation pressure causes unwrapping of the clamp section 81 (FIG. 28). The adhesive strips 101 are chosen so as to facilitate unwrapping of the clamp section 81 upon inflation.

The inflated clamp section 81 firmly grips the colonoscope 2, thereby preventing the entire device 100 being pulled out of the colon as the clinician 150 pulls the sheath 80 taut. The overtube 90 is then advanced over the colonoscope 2 into the sheath 80 in a manner similar to that described previously with reference to FIGS. 17 to 21.

To retract the device 100, the clamp section 81 is deflated and the sheath 80 is gently tugged to release the adhesive strip 102 from the colonoscope 2. The device 100 is then no longer secured to the colonoscope 2 and is then free to move relative to the colonoscope 2. The adhesive strip 102 is chosen so as to facilitate release upon application of a gentle tug on the sheath 80.

Retraction of the device 100 and further advancement of the colonoscope 2 through the colon proceeds in a manner similar to that described previously with reference to FIGS. 23 and 24.

It will be appreciated that other means of holding the clamp section 81 to the colonoscope 2 before insertion into a colon may be employed. For example the strips 101, 102 may be of a hook-and-pile material, such as Velcro.

Alternatively or additionally a drawstring may be used to releasably secure the clamp section 81 to the colonoscope 2, the drawstring being threaded back through the device 100 and/or the colonoscope 2 to facilitate proximal manipulation of the drawstring.

The insertion device according to the invention enables a stiffening overtube to be safely advanced over a colonoscope inserted into an accordioned sigmoid colon without the overtube engaging the inner wall of the sigmoid colon. In this manner friction between the overtube and the colon wall is eliminated. Thus a colonoscopy procedure may be performed more easily and more quickly, and without causing as much discomfort to the patient. In addition, there is no possibility that sections of the inner wall of the colon will become trapped between the colonoscope and the stiffening overtube.

The inflated clamp section maintains the device within the sigmoid colon during insertion of the overtube, even when tension is applied to pull the sheath taut. By pulling the sheath taut during insertion of the overtube formation of loops in the reduced sigmoid colon is prevented.

The distal end of the device is encapsulated by the distal fixation mechanism and is sealed from the environment of the colon during insertion into a colon. In this manner the distal fixation mechanism prevents any movement of the device relative to the colonoscope during the tortuous advancement through the sigmoid colon, including the reduction manoeuvre. In addition, the distal fixation mechanism prevents the influx of liquid or other material into the gap between the device and the colonoscope.

The insertion device and stiffening overtube apparatus provide a means of cannulating the colon. The device and stiffening overtube apparatus could also be applied to cannulate other body lumena, in which medical instruments are to be inserted.

In particular, the guide device and stiffening overtube apparatus could be used in upper GI endoscopy. It is often desirous to insert an overtube into the oesophagus over an endoscope so that a foreign body may be removed from the lower oesophagus or stomach without causing damage to the vocal chords. The overtube is slid over the endoscope in a manner similar to that in colonoscopy. The foreign body may then be pulled from the oesophagus or stomach without coming into contact with the vocal chords. However there is a danger to the vocal chords from the overtube as it slides down the endoscope during its introduction. This danger can be removed by the use of a sheath device mounted over the endoscope and between which the overtube can be passed in such a way that it does not come into direct contact with the vocal chords but is isolated from them by the presence of the overtube sheath.

The guide device and stiffening overtube apparatus could also be used in enteroscopy. This is an examination of the upper third of the small intestine carried out using a long endoscope that is introduced through the oesophagus and stomach. The cavernous nature of the stomach presents a similar situation to the endoscopist as found in colonoscopy with the mobile sigmoid colon. In this case a loop may form in the stomach and the problem can be addressed with the use of a stiffening overtube passed over the endoscope through the oesophagus. However there is a danger to the oesophagus and stomach from the leading edge of the overtube or the slit sides of the overtube and this can be removed by the use of an overtube sheath mounted to the endoscope and between which the overtube passes. In this case the device is deployed when the tip of the endoscope has passed through the pyloric valve at the distal end of the stomach and is firmly positioned within the proximal part of the duodenum.

The invention is not limited to the embodiments hereinbefore described which may be varied in detail.

What is claimed is:

1. An insertion device to aid introduction of at least one of a probe and an overtube into a passageway, the device comprising an elongate tubular sheath for extending through a passageway, the sheath defining a lumen to receive at least one of a probe and an overtube, and a holder to hold the sheath to at least one of a probe and an overtube,
   wherein the holder comprises a second holder for holding a probe to the sheath on insertion of an overtube into the sheath;
   wherein the second holder is movable from a release configuration to a probe engaging configuration; and
   wherein the second holder is movable by inflation from the release configuration to the probe engaging configuration.

2. A device as claimed in claim 1 wherein the sheath has a distal end and the holder is located at the distal end of the sheath.

3. A device as claimed in claim 1 wherein the holder comprises a first holder for holding the sheath to a probe on insertion of the probe into a passageway.

4. A device as claimed in claim 3 wherein the first holder is movable from a probe engaging configuration in which the first holder grips the probe to a release configuration in which a probe is movable relative to the first holder.

5. A device as claimed in claim 4 wherein the first holder comprises an adhesive strip.

6. A device as claimed in claim 4 wherein the first holder comprises a strip of a hook-and-pile material.

7. A device as claimed in claim 4 wherein the first holder comprises a band of a resilient material.

8. A device as claimed in claim 3 wherein the first holder comprises a drawstring.

9. A device as claimed in claim 8 wherein the drawstring is threaded back through at least one of the device and a probe received within the lumen to facilitate proximal manipulation thereof.

10. A device as claimed in claim 1 wherein the second holder comprises an inflatable tube, the tube having an inflation port for inflation of the tube.

11. A device as claimed in claim 10 wherein the inflation port has a connection means for connection to a supply of inflation fluid.

12. A device as claimed in claim 10 wherein the tube is integral with the sheath.

13. A device as claimed in claim 10 wherein the tube is attached to the sheath.

14. A device as claimed in claim 1, wherein the probe is an endoscope.

15. A device as claimed in claim 14, wherein the endoscope is one of a colonoscope, a gastroscope and an enteroscope.

16. A device as claimed in claim 1, wherein the probe has a tip and in the probe engaging configuration the tip extends distally of the sheath.

17. A method for carrying out at least one of an examination, a treatment and a diagnostic procedure comprising the steps of:
   providing a probe, an overtube for the probe and an insertion device to aid introduction of at least one of the probe and the overtube;
   mounting the insertion device to the probe;
   introducing the probe with the insertion device mounted thereto into a passageway;
   gripping the insertion device to the probe;
   introducing the overtube into the passageway between the probe and the insertion device;
   releasing the grip of the insertion device to the probe;
   removing the insertion device, and the overtube, and the probe from the passageway.

18. A method as claimed in claim 17 wherein the method comprises the step of holding the insertion device to the probe during introduction into a passageway.

19. A method as claimed in claim 18 wherein the method comprises the step of releasing the hold of the insertion device to the probe after introduction into a passageway and before gripping the insertion device to the probe.

20. A method as claimed in claim 19 wherein the hold is released by inflation of a portion of the insertion device.

21. A method as claimed in claim 17 wherein the insertion device is gripped to the probe by inflation of a portion of the insertion device.

22. A method as claimed in claim 17 wherein the method comprises the step of pulling the insertion device taut before introduction of the overtube between the probe and the insertion device.

23. A method as claimed in claim 17 wherein the insertion device is at least partially removed from the passageway after releasing the grip of the insertion device to the probe, and before removal of the overtube and the probe from the passageway.

24. A method as claimed in claim 17 wherein the probe comprises an endoscope.

25. A method as claimed in claim 24 wherein the endoscope comprises a colonoscope.

26. A method as claimed in claim 25 wherein the colonoscope with the insertion device mounted thereto is introduced into a colon to the start of the descending colon before introduction of the overtube.

27. A method as claimed in claim 25 wherein the colonoscope is advanced through the descending colon after introduction of the overtube.

28. A method as claimed in claim 27 wherein the insertion device is completely removed from the colon before advancing the colonoscope through the descending colon.

29. A method as claimed in claim 25 wherein the sigmoid colon is reduced to an accordioned configuration before introduction of the overtube.

* * * * *